US011634698B2

(12) United States Patent
Tan et al.

(10) Patent No.: US 11,634,698 B2
(45) Date of Patent: Apr. 25, 2023

(54) NUCLEASES AND METHODS FOR MAKING AND USING THEM

(71) Applicant: BASF SE, Ludwigshafen am Rhein (DE)

(72) Inventors: Xuqiu Tan, San Diego, CA (US); Kenneth Barrett, San Diego, CA (US); Jared Dennis, San Diego, CA (US); Dongmei Ren, San Diego, CA (US); Corey Dodge, San Diego, CA (US); Bin Zhang, San Diego, CA (US)

(73) Assignee: BASF SE, Ludwigshafen (DE)

( * ) Notice: Subject to any disclaimer, the term of this patent is extended or adjusted under 35 U.S.C. 154(b) by 124 days.

(21) Appl. No.: 16/954,276

(22) PCT Filed: Dec. 10, 2018

(86) PCT No.: PCT/US2018/064718
§ 371 (c)(1),
(2) Date: Jun. 16, 2020

(87) PCT Pub. No.: WO2019/125804
PCT Pub. Date: Jun. 27, 2019

(65) Prior Publication Data
US 2021/0139871 A1 May 13, 2021

Related U.S. Application Data

(60) Provisional application No. 62/608,201, filed on Dec. 20, 2017.

(51) Int. Cl.
| | |
|---|---|
| *C12N 9/22* | (2006.01) |
| *A23K 20/147* | (2016.01) |
| *A23K 20/189* | (2016.01) |
| *A23L 29/00* | (2016.01) |
| *A23L 33/18* | (2016.01) |
| *C11D 3/386* | (2006.01) |

(52) U.S. Cl.
CPC .............. *C12N 9/22* (2013.01); *A23K 20/147* (2016.05); *A23K 20/189* (2016.05); *A23L 29/06* (2016.08); *A23L 33/18* (2016.08); *C11D 3/38636* (2013.01); *C12Y 301/30002* (2013.01); *A23V 2002/00* (2013.01); *C07K 2319/02* (2013.01)

(58) Field of Classification Search
CPC . C12Y 301/30002; A23K 20/147; C12N 9/22
See application file for complete search history.

(56) References Cited

U.S. PATENT DOCUMENTS

| | | | |
|---|---|---|---|
| 5,830,696 A | 11/1998 | Short | |
| 6,340,566 B1 | 1/2002 | McCutchen-Maloney | |

FOREIGN PATENT DOCUMENTS

WO    WO2014/131113 A1    9/2014

OTHER PUBLICATIONS

Database EBI [Online] "Serratia marcescens endonuclease", Database accession No. OAH28326 (Feb. 15, 2016).
Database UniProt [Online] "SubName: Full=Endonuclease {ECO:0000313| AOE98765.1};" retrieved from EBI accession No. UNIPROT:A0A1B3FAD7 (Nov. 2, 2016).
International Search Report & Written Opinion ISA, PCT/US2018/064718 (dated Mar. 22, 2019).

*Primary Examiner* — Tekchand Saidha
(74) *Attorney, Agent, or Firm* — Marshall, Gerstein & Borun LLP

(57) ABSTRACT

Disclosed herein are polypeptides having nuclease activity. Some of the polypeptides having nuclease activity were generated by an improved gene site mutagenesis ("GSSM") method or the tailored multi-site combinatorial assembly ("TMCA") method. Also disclosed are compositions and kits comprising the polypeptides having nuclease activity, and methods for making and using these polypeptides, compositions and kits.

45 Claims, 5 Drawing Sheets
Specification includes a Sequence Listing.

ATGGCGCTTTAACAATAAAATGCTGGCACTTCGTAGCGCTGCTGTTTGCGGCGCAGGCCGTGTCCGCAGATACACTGGAGAGCATTGACAACTGCGCGTGGGCT 100

M  A  L  F  A  A  Q  A  S  A  D  T  L  E  S  I  D  N  C  A  V  G  33

GCCCGACCGGCGTTCTAGCAATGTTAGTATCGTCCGCCATGCGTATACTCTGAATAACAACTCCACCACCAAATTTGCCAACTGGGTGGCGTATCACAT 200

C  P  T  G  G  S  S  N  V  S  I  V  R  H  A  Y  T  L  N  N  S  T  K  F  A  N  W  V  A  Y  H  I  67

TACTAAAGACACACCTGCGTCAGGCAAGACTCGTAATTGGAAAACTGATCCAGCGTTGAATCCTGCTGACACCCTGGCTCCGGCGGATTATACCGGCGCT 300

T  K  D  T  P  A  S  G  K  T  R  N  W  K  T  D  P  A  L  N  P  A  D  T  L  A  P  A  D  Y  T  G  A  100

AATGCCGCTCTTAAAGTGGATCGTGGCCACCAGGCCCGCTTGCGAGCCTGTGTTTCAGACTGGGAAAGCCTGAATTACCTCTCAAACATCACGC 400

N  A  A  L  K  V  D  R  G  H  Q  A  P  L  A  S  L  A  G  V  S  D  W  E  S  L  N  Y  L  S  N  I  T  133

CGCAGAAAGTGACTGAATCAAGGCGCCGTGGGCCCGTCTGGAGGATCAGGAGCGCCAAACTTATCGATCGTGCAGATATTAGTAGTGTGTATACTGTCAC 500

P  Q  K  S  D  L  N  Q  G  A  W  A  R  L  E  D  Q  E  R  K  L  I  D  R  A  D  I  S  S  V  Y  T  V  T  167

GGGCCCACTGTACGAACGTGATATGGGCAAACTCCCGGGCACCCAGAAAGCTCACACTATTCCGTCTGCCTACTGGAAAGTGATCTTTATTAACAACTCC 600

G  P  L  Y  E  R  D  M  G  K  L  P  G  T  Q  K  A  H  T  I  P  S  A  Y  W  K  V  I  F  I  N  N  S  200

CCCGGCGGTGAATCATTACGCTGCGTTTTTGTTTGATCAGAACACCCCAAAAGGGGCGGATTTCTGCCAGTTTCGTGTTACCGTTGATGAAATTGAAAAAC 700

P  A  V  N  H  Y  A  A  F  L  F  D  Q  N  T  P  K  G  A  D  F  C  Q  F  R  V  T  V  D  E  I  E  K  233

GCACAGGCTTAATTATCTGGGCGGGCCTGCCAAATGACGTCCAGGCCGTCCTTGAAATCCAAGCCCGGGAACTGATGGGTTGCAAAAAC (SEQ ID NO: 2)

R  T  G  L  I  I  W  A  G  L  P  N  D  V  Q  A  S  L  K  S  K  P  G  V  L  P  E  L  M  G  C  K  N  (SEQ ID NO: 1)

FIG. 1

NUCLEASES AND METHODS FOR MAKING AND USING THEM

REFERENCE TO SEQUENCE LISTING

The present application is being filed along with a Sequence Listing in electronic format. The Sequence Listing is provided as a file entitled BASF_060_PR_SEQLISTING.TXT, created Dec. 20, 2017, which is 4 Kb in size. The information in the electronic format of the Sequence Listing is incorporated herein by reference in its entirety.

BACKGROUND

Field

The present disclosure relates generally to molecular and cellular biology and biochemistry. More specifically, the disclosure relates to polypeptides having nuclease activity, polynucleotides comprising the coding sequences for these polypeptides, and methods for making and using these polypeptides and polynucleotides.

Description of the Related Art

Nucleases are enzymes capable of cleaving the phosphodiester bonds between monomers of nucleic acids, so that they can process long-chain of nucleic acids into smaller units. Nucleases have been used widely in industrial and pharmaceutical applications. For example, the use of nucleases in fermentation processes can remove DNA, and facilitate and improve the production and recovery of proteins and other molecules of interest. DNA removal is important in fermentation processes since many of those processed utilize recombinant DNA technologies, and many applicable regulations require the confirmation of an absence of rDNA which can be removed by nucleases. Nucleases can also be used for biofilm removal, which has multiple applications, for example cleaning food machinery, hard surface cleaning, paper machines, wound healing, and oral care. There is a need for generating effective nucleases having desired optimal temperature and pH range.

SUMMARY

Disclosed herein includes polypeptides having nuclease activity (hereinafter "nucleases" or "nuclease polypeptides"), polynucleotides comprising the coding sequences for these polypeptides (hereafter "nuclease polynucleotides), and methods for making and using these polypeptides and polynucleotides. Also provided herein are compositions and kits comprising one or more of the nuclease polypeptides disclosed herein, one or more of the nuclease-coding polynucleotides, and any combination thereof.

Disclosed herein includes synthetic or recombinant polypeptide comprising an amino acid sequence having at least 80% sequence identity to SEQ ID NO: 1. In some embodiments, the polypeptide has nuclease activity, and wherein the polypeptide comprises one or more mutations of E230L, L114F, E260R, E230M, D246P, S161R, N54S, T227H, V226K, E230R, G263A, G119N, V226K, G263A, N127S, P84V, D83E, D28G, V45T, M262V, A190K, P84N, I44R, G256S, A73M, P179L, Q135E, A60P, V247I, G263K, S161E, P72N, P84L, S74N, T82R, G75R, Q141R, and D107N. In some embodiments, the amino acid sequence has at least 90% sequence identity to SEQ ID NO: 1. In some embodiments, the polypeptide comprises one or more mutations selected from the group consisting of L114F, G119N, D107N, S74N, Q141R, T82R, and G75R. In some embodiments, the polypeptide comprises a combination of mutations selected from the group consisting of:

(T82R, L114F);
(T82R, L114F, G119N);
(T82R)
(T82R, G119N);
(L114F);
(L114F, G119N);
(G119N);
(G75R, T82R, L114F, G119N);
(G75R, T82R, L114F, G119N);
(G75R, T82R);
(G75R, L114F);
(G75R, L114F, G119N);
(S74N, G75R, T82R, G119N, Q141R);
(S74N, T82R, L114F, G119N);
(S74N, T82R, L114F, G119N, Q141R);
(S74N, T82R, Q141R);
(S74N, T82R, G119N, Q141R);
(S74N, L114F, Q141R);
(S74N, L114F, G119N, Q141R);
(S74N, Q141R);
(S74N, G75R, T82R, L114F, Q141R);
(S74N, G75R, T82R, L114F, G119N, Q141R);
(S74N, G75R, T82R, Q141R);
(S74N, G75R, L114F, Q141R);
(S74N, G75R, Q141R);
(T82R, D107N);
(G75R, T82R, D107N);
(D107N);
(G75R, T82R, G119N);
(T82R, D107N, G119N);
(G75R, T82R, D107N, G119N);
(D107N, G119N);
(G75R, D107N, G119N);
(S74N, T82R, D107N, Q141R);
(S74N, G75R, T82R, D107N, Q141R);
(S74N, G75R, D107N, Q141R);
(S74N, G119N, Q141R);
(S74N, G75R, G119N, Q141R);
(S74N, T82R, D107N, G119N, Q141R);
(S74N, G75R, T82R, D107N, G119N, Q141R);
(S74N, D107N, G119N, Q141R);
(S74N, G75R, D107N, G119N, Q141R);
(T82R, D107N, L114F);
(G75R, T82R, D107N, L114F);
(D107N, L114F);
(G75R, D107N, L114F);
(G75R, D107N);
(T82R, D107N, L114F, G119N);
(D107N, L114F, G119N);
(G75R, D107N, L114F, G119N);
(S74N, T82R, D107N, L114F, Q141R);
(S74N, G75R, T82R, D107N, L114F, Q141R);
(S74N, D107N, L114F, Q141R);
(S74N, G75R, D107N, L114F, Q141R);
(S74N, D107N, Q141R);
(S74N, G75R, L114F, G119N, Q141R);
(S74N, T82R, D107N, L114F, G119N, Q141R);
(S74N, G75R, T82R, D107N, L114F, G119N, Q141R);
(S74N, D107N, L114F, G119N, Q141R);
(S74N, G75R, D107N, L114F, G119N, Q141R); and
(G75R, T82R, D107N, L114F, G119N).

In some embodiments, the amino acid sequence of the polypeptide differs from the amino acid sequence of SEQ ID NO: 1 for, or only for, comprising one or more mutations of E230L, L114F, E260R, E230M, D246P, S161R, N54S, T227H, V226K, E230R, G263A, G119N, V226K, G263A, N127S, P84V, D83E, D28G, V45T, M262V, A190K, P84N, I44R, G256S, A73M, P179L, Q135E, A60P, V247I, G263K, S161E, P72N, P84L, S74N, T82R, G75R, Q141R, and D107N.

In some embodiments, the polypeptide is more thermotolerant compared to the nuclease having the sequence of SEQ ID NO: 1. In some embodiments, the nuclease activity of the polypeptide is at least 5% higher than that of the nuclease having the sequence of SEQ ID NO: 1 at 10° C. to 70° C. In some embodiments, the nuclease activity of the polypeptide is at least 5% higher than that of the nuclease having the sequence of SEQ ID NO: 1 at 37° C. to 60° C. In some embodiments, the nuclease activity of the polypeptide is at least 5% higher than that of the nuclease having the sequence of SEQ ID NO: 1 at 40° C. to 60° C. In some embodiments, the nuclease activity ratio 54° C./37° C. of the polypeptide is at least 5% higher than that of the nuclease having the sequence of SEQ ID NO: 1. In some embodiments, the optimal temperature of the polypeptide is between 45° C. to 55° C. In some embodiments, the optimal pH of the polypeptide is between pH 4 to pH 11. In some embodiments, the polypeptide comprises no signal sequence. In some embodiments, the polypeptide comprises a signal sequence. In some embodiments, the signal sequence is a heterologous sequence.

Also disclosed herein includes a composition comprising one or more of the polypeptides disclosed herein. In some embodiments, the composition is a reaction mixture, a detergent composition, a detergent additive, a food, a food supplement, a feed supplement, a feed, a pharmaceutical composition, a fermentation product, a fermentation intermediate, a fermentation downstream reaction mixture, a reaction mixture, or a combination thereof. In some embodiments, the reaction mixture comprising one or more of the polypeptides is for protein expression or purification. For example, the polypeptide can be a polypeptide comprising an amino acid sequence having at least 80% sequence identity to SEQ ID NO: 1, where the polypeptide has nuclease activity, and where the polypeptide comprises one or more mutations of E230L, L114F, E260R, E230M, D246P, S161R, N54S, T227H, V226K, E230R, G263A, G119N, V226K, G263A, N127S, P84V, D83E, D28G, V45T, M262V, A190K, P84N, I44R, G256S, A73M, P179L, Q135E, A60P, V247I, G263K, S161E, P72N, P84L, S74N, T82R, G75R, Q141R, and D107N.

Also disclosed herein includes a synthetic or recombinant nucleic acid that encodes any one of the polypeptides disclosed herein, and an expression vector comprising the polynucleotide sequence of the synthetic or recombinant nucleic acid. In some embodiments, the expression vector comprises a viral vector, a plasmid, a phage, a phagemid, a cosmid, a fosmid, a bacteriophage, an artificial chromosome, or a combination thereof. For example, the polypeptide can be a polypeptide comprising an amino acid sequence having at least 80% sequence identity to SEQ ID NO: 1, where the polypeptide has nuclease activity, and where the polypeptide comprises one or more mutations of E230L, L114F, E260R, E230M, D246P, S161R, N54S, T227H, V226K, E230R, G263A, G119N, V226K, G263A, N127S, P84V, D83E, D28G, V45T, M262V, A190K, P84N, I44R, G256S, A73M, P179L, Q135E, A60P, V247I, G263K, S161E, P72N, P84L, S74N, T82R, G75R, Q141R, and D107N.

Disclosed herein includes a recombinant cell comprising one or more of the polypeptides disclosed herein, one or more synthetic or recombinant nucleic acid that encodes any one of the polypeptides disclosed herein, one or more expression vectors comprising the polynucleotide sequence of the synthetic or recombinant nucleic acid, or a combination thereof. In some embodiments, the nucleic acid is a part of a chromosome of the recombinant cell. In some embodiments, the recombinant cell is a bacterial cell, a mammalian cell, a fungal cell, a yeast cell, an insect cell, or a plant cell. For example, the polypeptide can be a polypeptide comprising an amino acid sequence having at least 80% sequence identity to SEQ ID NO: 1, where the polypeptide has nuclease activity, and where the polypeptide comprises one or more mutations of E230L, L114F, E260R, E230M, D246P, S161R, N54S, T227H, V226K, E230R, G263A, G119N, V226K, G263A, N127S, P84V, D83E, D28G, V45T, M262V, A190K, P84N, I44R, G256S, A73M, P179L, Q135E, A60P, V247I, G263K, S161E, P72N, P84L, S74N, T82R, G75R, Q141R, and D107N.

Disclosed herein includes a method of producing a recombinant polypeptide having nuclease activity. The method, in some embodiments, comprises: expressing the nucleic acid that encodes any one of the polypeptides disclosed herein under conditions that allow expression of the polypeptide, thereby producing recombinant polypeptide having nuclease activity, wherein the nucleic acid is operably linked to a promoter. In some embodiments, the nucleic acid is present in an expression vector. In some embodiments, the nucleic acid is present in a host cell to allow expression of the polypeptide. In some embodiments, the nucleic acid is present in a chromosome of the host cell. In some embodiments, the host cell is a cell from an organism selected from the group consisting of *Pichia pastoris* (*Komagataella pastoris*), *Bacillus subtilis*, *Pseudomonas fluorescens*, *Myceliopthora thermophile* fungus, *Tricodermea reesei*, *Escherichia coli*, *Bacillus licheniformis*, *Aspergillus niger*, *Schizosaccharomyces pombe*, and. *Sacaramyces cerevisiae*. In some embodiments, the nucleic acid is present an in vitro expression system. The polypeptide can be, in some embodiments, a polypeptide comprising an amino acid sequence having at least 80% sequence identity to SEQ ID NO: 1, where the polypeptide has nuclease activity, and where the polypeptide comprises one or more mutations of E230L, L114F, E260R, E230M, D246P, S161R, N54S, T227H, V226K, E230R, G263A, G119N, V226K, G263A, N127S, P84V, D83E, D28G, V45T, M262V, A190K, P84N, I44R, G256S, A73M, P179L, Q135E, A60P, V247I, G263K, S161E, P72N, P84L, S74N, T82R, G75R, Q141R, and D107N.

Disclosed herein includes a method for degrading a polynucleotide, comprising contacting a polynucleotide molecule with one or more of the polypeptides disclosed herein, thereby degrading the polynucleotide molecule. For example, the polypeptide can be a polypeptide comprising an amino acid sequence having at least 80% sequence identity to SEQ ID NO: 1, where the polypeptide has nuclease activity, and where the polypeptide comprises one or more mutations of E230L, L114F, E260R, E230M, D246P, S161R, N54S, T227H, V226K, E230R, G263A, G119N, V226K, G263A, N127S, P84V, D83E, D28G, V45T, M262V, A190K, P84N, I44R, G256S, A73M, P179L, Q135E, A60P, V247I, G263K, S161E, P72N, P84L, S74N, T82R, G75R, Q141R, and D107N. In some embodiments, the polynucleotide molecule is a DNA molecule or a RNA molecule. In some embodiments, the contacting occurs at pH 4 to pH 11. In some embodiments, the reaction mixture has a temperature at about 10° C. to about 70° C. In some embodiments, the contacting occurs at 40° C. to 60° C.

Disclosed herein includes a method for washing an object. The method, in some embodiments, comprises contacting a composition comprising one or more of the polypeptides disclosed herein with the object under the conditions sufficient for said washing. In some embodiments, the polypeptide comprises an amino acid sequence having at least 80% sequence identity to SEQ ID NO: 1, wherein the polypeptide has nuclease activity, and wherein the polypeptide comprises one or more mutations of E230L, L114F, E260R, E230M, D246P, S161R, N54S, T227H, V226K, E230R, G263A, G119N, V226K, G263A, N127S, P84V, D83E, D28G, V45T, M262V, A190K, P84N, I44R, G256S, A73M, P179L, Q135E, A60P, V247I, G263K, S161E, P72N, P84L, S74N, T82R, G75R, Q141R, and D107N. In some embodiments, the object is a textile.

Also disclosed herein includes a method for degrading DNA or RNA during protein production. The method, in some embodiments, comprises culturing a host cell, wherein the host cell comprises a nucleic acid encoding a protein of interest; and expressing one or more of the polypeptides disclosed herein under conditions that allow degradation of DNA or RNA by the one or more polypeptides. In some embodiments, the host cell is a bacterial cell, a mammalian cell, a fungal cell, a yeast cell, a plant cell, or an insect cell. In some embodiments, the polypeptide is expressed from an expression vector present in the host cell or the polypeptide is encoded by a nucleic acid sequence in a chromosome of the host cell. In some embodiments, the polypeptide is expressed by cells that do not express the protein of interest. In some embodiments, expression of one or more of the protein of interest and the polypeptide is inducible or non-inducible. In some embodiments, one or more of the polypeptides disclosed herein are added externally. For example, the polypeptide can be a polypeptide comprising an amino acid sequence having at least 80% sequence identity to SEQ ID NO: 1, where the polypeptide has nuclease activity, and where the polypeptide comprises one or more mutations of E230L, L114F, E260R, E230M, D246P, S161R, N54S, T227H, V226K, E230R, G263A, G119N, V226K, G263A, N127S, P84V, D83E, D28G, V45T, M262V, A190K, P84N, I44R, G256S, A73M, P179L, Q135E, A60P, V247I, G263K, S161E, P72N, P84L, S74N, T82R, G75R, Q141R, and D107N.

Also disclose herein include a reaction mixture, wherein the reaction mixture comprises: (a) one or more of the polypeptides disclosed herein, (b) one or more nucleic acid molecules, and (c) an aqueous solution wherein the polypeptide hydrolyzes the one or more nucleic acid molecules. In some embodiments, the one or more nucleic acid molecules comprise single-stranded DNA molecules, double-stranded DNA molecules, single-stranded RNA molecules, double-stranded RNA molecules, or any combination thereof. In some embodiments, the one or more nucleic acid molecules are from a host cell for protein production. In some embodiments, the polypeptide is expressed in a host cell selected from the group consisting of a bacterial cell, a mammalian cell, a fungal cell, a yeast cell, and an insect cell. In some embodiments, the reaction mixture has a temperature at about 10° C. to about 70° C. In some embodiments, the reaction mixture has a temperature at about 45° C. to about 55° C. In some embodiments, the reaction mixture is at about pH 4 to about pH 11. In some embodiments, the reaction mixture is at about pH 6 to about pH 7. In some embodiments, the aqueous solution is a detergent composition, a detergent additive, a food, a food supplement, a feed supplement, a feed, a pharmaceutical composition, a fermentation product, a fermentation intermediate, a fermentation downstream reaction mixture, a product from protein production process, an intermediate from protein production process, a protein purification solution, or a combination thereof. For example, the polypeptide can be a polypeptide comprising an amino acid sequence having at least 80% sequence identity to SEQ ID NO: 1, where the polypeptide has nuclease activity, and where the polypeptide comprises one or more mutations of E230L, L114F, E260R, E230M, D246P, S161R, N54S, T227H, V226K, E230R, G263A, G119N, V226K, G263A, N127S, P84V, D83E, D28G, V45T, M262V, A190K, P84N, I44R, G256S, A73M, P179L, Q135E, A60P, V247I, G263K, S161E, P72N, P84L, S74N, T82R, G75R, Q141R, and D107N.

Disclosed herein include a method for degrading DNA or RNA in a protein production mixture. The method comprises, in some embodiments, culturing a host cell which comprises a nucleic acid encoding a protein of interest; and expressing one or more of the polypeptides disclosed herein under conditions that allow degradation of DNA or RNA by the polypeptide. The expression of the polypeptide can be delayed, in some embodiments, until after the production of the protein of interest. In some embodiments, the expression of the polypeptide is not delayed. The expression of the polypeptide can start before, after, or at the same time with the start of the expression of the protein of interest. The host cell can be, for example, a bacterial cell, a mammalian cell, a fungal cell, a yeast cell, a plant cell, or an insect cell. In some embodiments, the polypeptide is expressed from an expression vector present in the host cell or the polypeptide is encoded by a nucleic acid sequence in a chromosome of the host cell. In some embodiments, the polypeptide is expressed by cells that do not express the protein of interest. The expression of one or more of the protein of interest and the polypeptides can be inducible or non-inducible.

Also disclosed herein include a method for degrading DNA or RNA during protein production. The method comprises, in some embodiments, culturing a host cell that comprises a nucleic acid encoding a protein of interest; and adding a polypeptide disclosed herein under conditions that allow degradation of DNA or RNA by the polypeptide. The host cell can be, for example, a bacterial cell, a mammalian cell, a fungal cell, a yeast cell, a plant cell, or an insect cell.

BRIEF DESCRIPTION OF THE DRAWINGS

FIG. 1 shows the protein sequence of the nuclease having the sequence of SEQ ID NO: 1 and the corresponding nucleic acid coding sequence (SEQ ID NO: 2).

DETAILED DESCRIPTION

Figure 2:
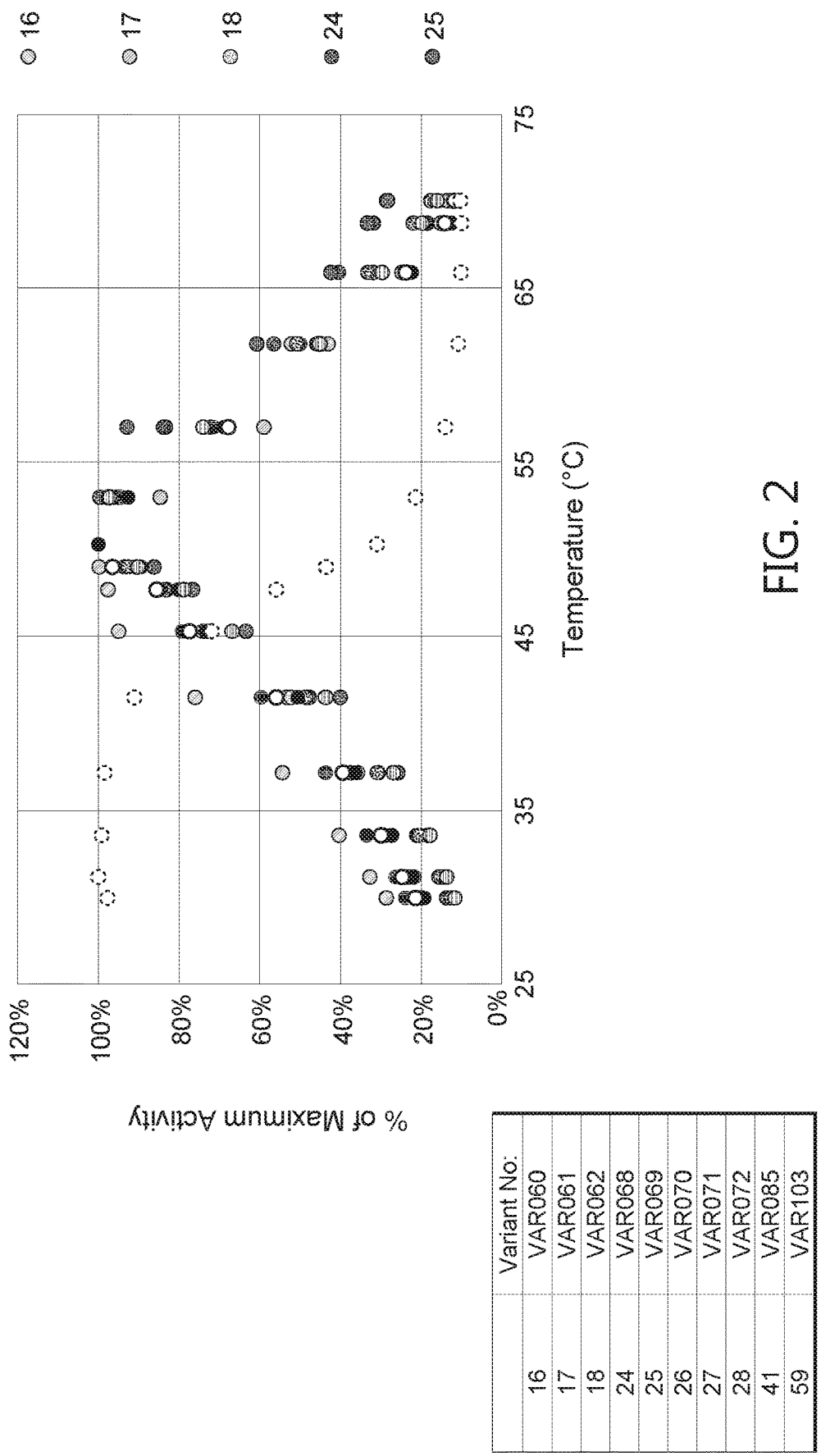
FIG. 2 shows temperature profiling of ten nuclease variants.

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, the singular forms "a", "an", and "the" include plural references unless indicated otherwise, expressly or by context. For example, "a" dimer includes one or more dimers, unless indicated otherwise, expressly or by context.

The term "amplification" ("a polymerase extension reaction") means that the number of copies of a polynucleotide is increased.

As used herein, "sequence identity" or "identity" in the context of two protein sequences (or nucleotide sequences) includes reference to the residues in the two sequences which are the same when aligned for maximum correspondence over a specified comparison window.

Sequence identity usually is provided as "% sequence identity" or "% identity". To determine the percent-identity between two amino acid sequences in a first step a pairwise sequence alignment is generated between those two sequences, wherein the two sequences are aligned over their complete length (i.e., a pairwise global alignment). The alignment is generated with a program implementing the Needleman and Wunsch algorithm (J. Mol. Biol. (1979) 48, p. 443-453), preferably by using the program "NEEDLE" (The European Molecular Biology Open Software Suite (EMBOSS)) with the programs default parameters (gapopen=10.0, gapextend=0.5 and matrix=EBLOSUM62). The preferred alignment for the purpose of this description is that alignment, from which the highest sequence identity can be determined.

After aligning two sequences, in a second step, an identity value is determined from the alignment produced. For purposes of this description, percent identity is calculated by:

%-identity=(identical residues/length of the alignment region which is showing the respective sequence of this description over its complete length)*100.

Thus, sequence identity in relation to comparison of two amino acid sequences according to this embodiment is calculated by dividing the number of identical residues by the length of the alignment region which is showing the respective sequence of this description over its complete length. This value is multiplied with 100 to give "%-identity".

For calculating the percent identity of two DNA sequences the same applies as for the calculation of percent identity of two amino acid sequences with some specifications.

For DNA sequences encoding for a protein the pairwise alignment shall be made over the complete length of the coding region from start to stop codon excluding introns. Introns, present in the other sequence, so the sequence to which the sequence of this description is compared, may also be removed for the pairwise alignment. Percent identity is then calculated by: %-identity=(identical residues/length of the alignment region which is showing the coding region of the sequence of this description from start to stop codon excluding introns over its complete length)*100.

For non-protein-coding DNA sequences the pairwise alignment shall be made over the complete length of the sequence of this description, so percent identity is calculated by: %-identity=(identical residues/length of the alignment region which is showing the sequence of this description over its complete length)*100.

Moreover, the preferred alignment program implementing the Needleman and Wunsch algorithm (J. Mol. Biol. (1979) 48, p. 443-453) is "NEEDLE" (The European Molecular Biology Open Software Suite (EMBOSS)) with the programs default parameters (gapopen=10.0, gapextend=0.5 and matrix=EDNAFULL).

Sequences, having identical or similar regions with a sequence of this description, and which shall be compared with a sequence of this description to determine % identity, can easily be identified by various ways that are within the skill in the art, for instance, using publicly available computer methods and programs such as BLAST, BLAST-2, available for example at NCBI.

Variants of the parent enzyme molecules may have an amino acid sequence which is at least n percent identical to the amino acid sequence of the respective parent enzyme having enzymatic activity with n being an integer between 50 and 100, preferably 50, 55, 60, 65, 70, 75, 80, 85, 90, 91, 92, 93, 94, 95, 96, 97, 98 or 99 compared to the full length polypeptide sequence. Preferably, variant enzymes which are n percent identical when compared to a parent enzyme, have enzymatic activity.

Enzyme variants may be defined by their sequence similarity when compared to a parent enzyme. Sequence similarity usually is provided as "% sequence similarity" or "%-similarity". For calculating sequence similarity in a first step a sequence alignment has to be generated as described above. In a second step, the percent-similarity has to be calculated, whereas percent sequence similarity takes into account that defined sets of amino acids share similar properties, e.g., by their size, by their hydrophobicity, by their charge, or by other characteristics. Herein, the exchange of one amino acid with a similar amino acid is called "conservative mutation". Enzyme variants comprising conservative mutations appear to have a minimal effect on protein folding resulting in certain enzyme properties being substantially maintained when compared to the enzyme properties of the parent enzyme.

For determination of %-similarity according to this description the following applies, which is also in accordance with the BLOSUM62 matrix as for example used by program "NEEDLE", which is one of the most used amino acids similarity matrix for database searching and sequence alignments.

Amino acid A is similar to amino acids S;
Amino acid D is similar to amino acids E; N;
Amino acid E is similar to amino acids D; K; Q;
Amino acid F is similar to amino acids W; Y;
Amino acid H is similar to amino acids N; Y;
Amino acid I is similar to amino acids L; M; V;
Amino acid K is similar to amino acids E; Q; R;
Amino acid L is similar to amino acids I; M; V;
Amino acid M is similar to amino acids I; L; V;
Amino acid N is similar to amino acids D; H; S;
Amino acid Q is similar to amino acids E; K; R;
Amino acid R is similar to amino acids K; Q;
Amino acid S is similar to amino acids A; N; T;

Amino acid T is similar to amino acids S;
Amino acid V is similar to amino acids I; L; M;
Amino acid W is similar to amino acids F; Y; and
Amino acid Y is similar to amino acids F; H; W.

Conservative amino acid substitutions may occur over the full length of the sequence of a polypeptide sequence of a functional protein such as an enzyme. In one embodiment, such mutations are not pertaining the functional domains of an enzyme. In one embodiment, conservative mutations are not pertaining the catalytic centers of an enzyme.

Therefore, according to the present description the following calculation of percent-similarity applies:

%-similarity=[(identical residues+similar residues)/
length of the alignment region which is showing the respective sequence of this description over its complete length]*100.

Especially, variant enzymes comprising conservative mutations which are at least m % similar to the respective parent sequences with m being an integer between 50 and 100, preferably 50, 55, 60, 65, 70, 75, 80, 85, 90, 91, 92, 93, 94, 95, 96, 97, 98 or 99 compared to the full-length polypeptide sequence, are expected to have essentially unchanged enzyme properties. Preferably, variant enzymes with m %-similarity when compared to a parent enzyme, have enzymatic activity.

Homologous refers to a gene, polypeptide, polynucleotide with a high degree of similarity, e.g. in position, structure, function or characteristic, but not necessarily with a high degree of sequence identity.

As used herein, "substantially complementary or substantially matched" means that two nucleic acid sequences have at least about 90% sequence identity. Preferably, the two nucleic acid sequences have at least, or at least about, 95%, 96%, 97%, 98%, 99%, or 100% of sequence identity. Alternatively, "substantially complementary or substantially matched" means that two nucleic acid sequences can hybridize under high stringency condition(s).

The term "hybridization" as defined herein is a process wherein substantially complementary nucleotide sequences anneal to each other. The hybridization process can occur entirely in solution, i.e. both complementary nucleic acids are in solution. The hybridization process can also occur with one of the complementary nucleic acids immobilized to a matrix such as magnetic beads, Sepharose beads or any other resin. The hybridization process can furthermore occur with one of the complementary nucleic acids immobilized to a solid support such as a nitro-cellulose or nylon membrane or immobilized by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids. Hybridization according to this description means, that hybridization must occur over complete length of the sequence of the invention. Such hybridization over the complete length, as defined herein, means, that when the sequence of this invention is fragmented into pieces of 300-500 bases, each fragment will hybridize The term "stringency" refers to the conditions under which a hybridization takes place. The stringency of hybridization is influenced by conditions such as temperature, salt concentration, ionic strength and hybridization buffer composition. Generally, low stringency conditions are selected to be about 30° C. lower than the thermal melting point (Tm) for the specific sequence at a defined ionic strength and ph.

Medium stringency conditions are when the temperature is 20° C. below Tm, and high stringency conditions are when the temperature is 10° C. below Tm. High stringency hybridization conditions are typically used for isolating hybridizing sequences that have high sequence identity to the target nucleic acid sequence. However, nucleic acids may deviate in sequence and still encode a substantially identical polypeptide, due to the degeneracy of the genetic code. Therefore, medium stringency hybridization conditions may sometimes be needed to identify such nucleic acid molecules. The "Tm" is the temperature under defined ionic strength and pH, at which 50% of the target sequence hybridizes to a perfectly matched probe. The Tm is dependent upon the solution conditions and the base composition and length of the probe. For example, longer sequences hybridize specifically at higher temperatures. The maximum rate of hybridization is obtained from about 16° C. up to 32° C. below Tm. The presence of monovalent cations in the hybridization solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridization to be performed at 30 to 45° C., though the rate of hybridisation will be lowered. Base pair mismatches reduce the hybridization rate and the thermal stability of the duplexes. On average and for large probes, the Tm decreases about 1° C. per % base mismatch. The Tm may be calculated using the following equations, depending on the types of hybrids:

DNA-DNA hybrids (Meinkoth and Wahl, Anal. Biochem., 138: 267-284, 1984):

$$T_m = 81.5° C. + 16.6 \times \log[Na^+]^a + 0.41 \times \%[G/C^b] - 500 \times [L^c]^{-1} - 0.61 \times \% \text{ formamide}$$

DNA-RNA or RNA-RNA hybrids:

$$T_m = 79.8 + 18.5(\log_{10}[Na^+]^a + 0.58(\% G/C^b) + 11.8(\% G/C^b)^2 - 820/L^c$$

oligo-DNA or oligo-RNAs hybrids:
For <20 nucleotides: $T_m = 2 (l_n)$
For 20-35 nucleotides: $T_m = 22 + 1.46 (l_n)$

[a] or for other monovalent cation, but only accurate in the 0.01-0.4 M range.
[b] only accurate for % GC in the 30% to 75% range.
[c] L=length of duplex in base pairs.
[d] Oligo, oligonucleotide; $l_n$, effective length of primer=2× (no. of G/C)+(no. of A/T).

Non-specific binding may be controlled using any one of a number of known techniques such as, for example, blocking the membrane with protein containing solutions, additions of heterologous RNA, DNA, and SDS to the hybridization buffer, and treatment with RNase. For non-related probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridization and which will either maintain or change the stringency conditions.

Besides the hybridization conditions, specificity of hybridization typically also depends on the function of post-hybridization washes. To remove background resulting from non-specific hybridization, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridization stringency. A positive hybridization gives a signal that is at least twice of that of the background. Generally, suitable stringent conditions for nucleic acid hybridization assays or gene amplification detection procedures are as set forth above. More or less stringent conditions may also be selected. The skilled artisan is aware of various parameters which may be altered during washing and which will either maintain or change the stringency conditions.

For example, typical high stringency hybridization conditions for DNA hybrids longer than 50 nucleotides encompass hybridization at 65° C. in 1×SSC or at 42° C. in 1×SSC and 50% formamide, followed by washing at 65° C. in 0.3×SSC. Examples of medium stringency hybridization conditions for DNA hybrids longer than 50 nucleotides encompass hybridization at 50° C. in 4×SSC or at 40° C. in 6×SSC and 50% formamide, followed by washing at 50° C. in 2×SSC. The length of the hybrid is the anticipated length for the hybridizing nucleic acid. When nucleic acids of known sequence are hybridized, the hybrid length may be determined by aligning the sequences and identifying the conserved regions described herein. 1×SSC is 0.15M NaCl and 15 mM sodium citrate; the hybridization solution and wash solutions may additionally include 5×Denhardt's reagent, 0.5-1.0% SDS, 100 µg/ml denatured, fragmented salmon sperm DNA, 0.5% sodium pyrophosphate. Another example of high stringency conditions is hybridization at 65° C. in 0.1×SSC comprising 0.1 SDS and optionally 5×Denhardt's reagent, 100 µg/ml denatured, fragmented salmon sperm DNA, 0.5% sodium pyrophosphate, followed by the washing at 65° C. in 0.3×SSC.

For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

As used herein, a "primer" refers to a nucleic acid molecule that can anneal to a template nucleic acid and serves as a starting point for DNA amplification. The primer can be entirely or partially complementary to a specific region of the template polynucleotide, for example 20 nucleotides upstream or downstream from a codon of interest. A non-complementary nucleotide is defined herein as a mismatch. A mismatch may be located within the primer or at the either end of the primer. Preferably, a single nucleotide mismatch, more preferably two, and more preferably, three or more consecutive or not consecutive nucleotide mismatches is (are) located within the primer. The primer can have, for example, from 5 to 200 nucleotides, preferably, from 20 to 80 nucleotides, and more preferably, from 43 to 65 nucleotides. More preferably, the primer has 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, or 190 nucleotides. A "forward primer" as defined herein is a primer that is complementary to a minus strand of the template polynucleotide. A "reverse primer" as defined herein is a primer complementary to a plus strand of the template polynucleotide. Preferably, the forward and reverse primers do not comprise overlapping nucleotide sequences. "Do not comprise overlapping nucleotide sequences" as defined herein means that a forward and reverse primer does not anneal to a region of the minus and plus strands, respectively, of the template polynucleotide in which the plus and minus strands are complimentary to one another. With regard to the primers annealing to the same strand of the template polynucleotide, "do not comprise overlapping nucleotide sequences" means the primers do not comprise sequences complementary to the same region of the same strand of the template polynucleotide. As used herein, a "primer set" refers to a combination of a "forward primer" and a corresponding "reverse primer."

As used herein, the plus strand equivalent to the sense strand and may also be referred to as a coding or non-template strand. This is the strand that has the same sequence as the mRNA (except it has Ts instead of Us). The other strand, called the template, minus, or antisense strand, is complementary to the mRNA.

As described herein, "codon optimization" refers to the design process of altering codons to codons known to increase maximum protein expression efficiency. In some alternatives, codon optimization for expression in a cell is described, wherein codon optimization can be performed by using algorithms that are known to those skilled in the art so as to create synthetic genetic transcripts optimized for high mRNA and protein yield in a host cell of interest, for example bacterial, fungal, insect, or mammalian cells (including human cells). Codons can be optimized for protein expression in a bacterial cell, mammalian cell, yeast cell, insect cell, or plant cell, for example. Programs containing algorithms for codon optimization in human cells are readily available. Such programs can include, for example, OptimumGene™ or GeneGPS® algorithms. Additionally codon optimized sequences can be obtained commercially, for example, from Integrated DNA Technologies. In some embodiments, the genes are codon optimized for expression in bacterial, yeast, fungal or insect cells.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction may be electrophoresed on a gel.

An enzyme is a biological molecule comprising a sequence of amino acids, wherein the enzyme can catalyze a reaction. Enzyme names are known to those skilled in the art based on the recommendations of the Nomenclature Committee of the International Union of Biochemistry and Molecular Biology (IUBMB). Enzyme names include: an EC (Enzyme Commission) number, recommended name, alternative names (if any), catalytic activity, and other factors. An enzyme is also known as a polypeptide, a protein, a peptide, an amino acid sequence, or is identified by a SEQ ID NO. In this disclosure, the alternative names for enzyme can be used interchangeably.

The term "heterologous" (or exogenous or foreign or recombinant) polypeptide is defined herein as:
(a) a polypeptide that is not native to the host cell. The protein sequence of such a heterologous polypeptide is a synthetic, non-naturally occurring, "man made" protein sequence;
(b) a polypeptide native to the host cell in which structural modifications, e.g., deletions, substitutions, and/or insertions, have been made to alter the native polypeptide; or
(c) a polypeptide native to the host cell whose expression is quantitatively altered or whose expression is directed from a genomic location different from the native host cell as a result of manipulation of the DNA of the host cell by recombinant DNA techniques, e.g., a stronger promoter.

Descriptions b) and c), above, refer to a sequence in its natural form but not naturally expressed by the cell used for its production. The produced polypeptide is therefore more precisely defined as a "recombinantly expressed endogenous polypeptide", which is not in contradiction to the above definition but reflects the specific situation that it's not the sequence of a protein being synthetic or manipulated but the way the polypeptide molecule is produced.

Similarly, the term "heterologous" (or exogenous or foreign or recombinant) polynucleotide refers:
(a) to a polynucleotide that is not native to the host cell;
(b) a polynucleotide native to the host cell in which structural modifications, e.g., deletions, substitutions, and/or insertions, have been made to alter the native polynucleotide;
(c) a polynucleotide native to the host cell whose expression is quantitatively altered as a result of manipulation of the regulatory elements of the polynucleotide by recombinant DNA techniques, e.g., a stronger promoter; or
(d) a polynucleotide native to the host cell, but integrated not within its natural genetic environment as a result of genetic manipulation by recombinant DNA techniques.

With respect to two or more polynucleotide sequences or two or more amino acid sequences, the term "heterologous" is used to characterize that the two or more polynucleotide sequences or two or more amino acid sequences do not occur naturally in the specific combination with each other.

As used herein, "transgenic", "transgene" or "recombinant" means with regard to, for example, a nucleic acid sequence, an expression cassette, genetic construct or a vector comprising the nucleic acid sequence or an organism transformed with the nucleic acid sequences, expression cassettes or vectors, all those constructions brought about synthetically by recombinant or genetechnological methods in which either
(a) the nucleic acid sequences comprising desired genetic information to be expressed, or
(b) genetic control sequence(s) which is operably linked with the nucleic acid sequence comprising said desired genetic information, for example a promoter, or
(c) both (a) and (b),
are not located in their natural genetic environment or have been modified by recombinant methods. The natural genetic environment is understood as meaning the natural genomic or chromosomal locus in the original organism. A naturally occurring expression cassette—for example the naturally occurring combination of the natural promoter of the nucleic acid sequences with the corresponding nucleic acid sequence encoding a polypeptide, becomes a transgenic expression cassette when this expression cassette is modified through human intervention such as, for example, mutagenic treatment. Suitable methods are described, for example, in U.S. Pat. No. 5,565,350, US200405323 and WO 00/15815. Furthermore, a naturally occurring expression cassette becomes a recombinant expression cassette when this expression cassette is isolated from its natural genetic environment and subsequently reintroduced in a genetic environment that is not the natural genetic environment.

A "synthetic" or "artificial" compound is produced by in vitro chemical or enzymatic synthesis. It includes, but is not limited to, variant nucleic acids made with optimal codon usage for host organisms, such as a yeast cell host or other expression hosts of choice or variant protein sequences with amino acid modifications, such as e.g. substitutions, compared to the parent protein sequence—e.g. to optimize properties of the polypeptide.

The term "restriction site" refers to a recognition sequence that is necessary for the manifestation of the action of a restriction enzyme, and includes a site of catalytic cleavage. It is appreciated that a site of cleavage may or may not be contained within a portion of a restriction site that comprises a low ambiguity sequence (i.e. a sequence containing the principal determinant of the frequency of occurrence of the restriction site). Thus, in many cases, relevant restriction sites contain only a low ambiguity sequence with an internal cleavage site (e.g. G/AATTC in the EcoRI site) or an immediately adjacent cleavage site (e.g. /CCWGG in the EcoRII site). In other cases, relevant restriction enzymes (e.g. the Eco57I site or CTGAAG(16/14)) contain a low ambiguity sequence (e.g. the CTGAAG sequence in the Eco57I site) with an external cleavage site (e.g. in the N16 portion of the Eco57I site). When an enzyme (e.g. a restriction enzyme) is said to "cleave" a polynucleotide, it is understood to mean that the restriction enzyme catalyzes or facilitates a cleavage of a polynucleotide.

An "ambiguous base requirement" in a restriction site refers to a nucleotide base requirement that is not specified to the fullest extent, i.e. that is not a specific base (such as, in a non-limiting exemplification, a specific base selected from A, C, G and T), but rather may be any one of at least two or more bases. Commonly accepted abbreviations that are used in the art as well as herein to represent ambiguity in bases include the following: R=G or A; Y=C or T; M=A or C; K=G or T; S=G or C; W=A or T; H=A or C or T; B=G or T or C; V=G or C or A; D=G or A or T; N=A or C or G or T.

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith (Smith and Waterman, Adv Appl Math, 1981; Smith and Waterman, J Teor Biol, 1981; Smith and Waterman, J Mol Biol, 1981; Smith et al, J Mol Evol, 1981), by the homology alignment algorithm of Needleman (Needleman and Wuncsch, 1970), by the search of similarity method of Pearson (Pearson and Lipman, 1988), by computerized implementations of these algorithms BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The terms "fragment", "derivative" and "analog" when referring to a reference polypeptide comprise a polypeptide which retains at least one biological function or activity that is at least essentially same as that of the reference polypeptide.

The term "functional fragment" refers to any nucleic acid or amino acid sequence which comprises merely a part of the full length nucleic acid or full length amino acid sequence, respectively, but still has the same or similar activity and/or function. In one embodiment, the fragment comprises at least 70%, at least 80%, at least 85%, at least 90%, at least 95%, at least 96%, at least 97%, at least 98%, at least 99% of the original sequence. In one embodiment, the functional fragment comprises contiguous nucleic acids or amino acids compared to the original nucleic acid or original amino acid sequence, respectively.

The term "pro-form", "pro-protein", or "pro-peptide", refers to a protein precursor, which is an inactive or low activity protein (or peptide) that can be turned into an active or more active form by post-translational modification, such by cleavage or by addition of another peptide or molecule, to produce a mature protein (e.g., to form an enzyme from a pro-enzyme).

The term "gene" means the segment of DNA involved in producing a polypeptide chain; it includes regions preceding and following the coding region (leader and trailer) as well as optionally intervening sequences (introns) between individual coding segments (exons).

As used herein, the term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment. As further example, an isolated nucleic acid, e.g., a DNA or RNA molecule, is one that is not immediately contiguous with the 5' and 3' flanking sequences with which it normally is immediately contiguous when present in the naturally occurring genome of the organism from which it is derived. Such polynucleotides could be part of a vector, incorporated into a genome of a cell with an unrelated genetic background (or into the genome of a cell with an essentially similar genetic background, but at a site different from that at which it naturally occurs), or produced by PCR amplification or restriction enzyme digestion, or an RNA molecule produced by in vitro transcription, and/or such polynucleotides, polypeptides, or enzymes could be part of a composition, and still be isolated in that such vector or composition is not part of its natural environment.

The term "isolated" means that the DNA is incorporated into a vector, such as a plasmid or viral vector; a nucleic acid that is incorporated into the genome of a heterologous cell (or the genome of a homologous cell, but at a non-naturally occurring site); and a nucleic acid that exists as a separate molecule, e.g., a DNA fragment produced by PCR amplification or restriction enzyme digestion, or an RNA molecule produced by in vitro transcription.

As used herein, the term "purified" does not require absolute purity; rather, it is intended as a relative definition. Individual nucleic acids obtained from a library have been conventionally purified to electrophoretic homogeneity. For example, the purified nucleic acids of the present disclosure can be purified from the remainder of the genomic DNA in the organism by at least $10^4$-$10^6$ fold. However, the term "purified" also includes nucleic acids which have been purified from the remainder of the genomic DNA or from other sequences in a library or other environment by at least one order of magnitude, typically two or three orders, and more typically four or five orders of magnitude "Purified" means that the material is in a relatively pure state, e.g., at least about 90% pure, at least about 95% pure, or at least about 98% or 99% pure. Preferably "purified" means that the material is in a 100% pure state.

The term "operably linked" means that the described components are in a relationship permitting them to function in their intended manner. For example, a regulatory sequence operably linked to a coding sequence is ligated in such a way that expression of the coding sequence is achieved under condition compatible with the control sequences. As used herein, a promoter sequence is "operably linked to" a coding sequence when RNA polymerase which initiates transcription at the promoter can transcribe the coding sequence into mRNA.

The term "mutations" is defined as alterations in the genetic code of nucleic acid sequence or alterations in the sequence of a peptide. Such mutations may be point mutations such as transitions or transversions. A mutation may be a change to one or more nucleotides or encoded amino acid sequences. The mutations may be deletions, insertions or duplications.

The terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

For nucleotide sequences, e.g., consensus sequences, an IUPAC nucleotide nomenclature (Nomenclature Committee of the International Union of Biochemistry (NC-IUB) (1984). "Nomenclature for Incompletely Specified Bases in Nucleic Acid Sequences".) is used, with the following nucleotide and nucleotide ambiguity definitions, relevant to this description: A, adenine; C, cytosine; G, guanine; T, thymine; K, guanine or thymine; R, adenine or guanine; W, adenine or thymine; M, adenine or cytosine; Y, cytosine or thymine; D, not a cytosine; N, any nucleotide.

In addition, notation "N(3-5)" means that indicated consensus position may have 3 to 5 any (N) nucleotides. For example, a consensus sequence "AWN(4-6)" represents 3 possible variants—with 4, 5, or 6 any nucleotides at the end: AWNNNN, AWNNNNN, AWNNNNNN.

The terms "nucleic acid sequence coding for" or a "DNA coding sequence of" or a "nucleotide sequence encoding" a particular protein or polypeptide refer to a DNA sequence which is transcribed and translated into a protein or polypeptide when placed under the control of appropriate regulatory sequences.

The terms "nucleic acid encoding a protein or peptide" or "DNA encoding a protein or peptide" or "polynucleotide encoding a protein or peptide" and other synonymous terms encompasses a polynucleotide which includes only coding sequence for the protein or peptide as well as a polynucleotide which includes additional coding and/or non-coding sequence.

The terms "regulatory element", "control sequence" and "promoter" are all used interchangeably herein and are to be taken in a broad context to refer to regulatory nucleic acid sequences capable of effecting expression of the sequences to which they are associated. "Regulatory elements" or "regulatory nucleotide sequences" herein may mean pieces of nucleic acid which drive expression of a nucleic acid sequence. upon transformation into a host cell or cell organelle had occurred. Regulatory nucleotide sequences may include any nucleotide sequence having a function or purpose individually and within a particular arrangement or grouping of other elements or sequences within the arrangement. Examples of regulatory nucleotide sequences include but are not limited to transcription control elements such as promoters, enhancers, and termination elements. Regulatory nucleotide sequences may be native (i.e. from the same gene) or foreign (i.e. from a different gene) to a nucleotide sequence to be expressed.

The term "promoter" typically refers to a nucleic acid control sequence located upstream from the transcriptional start of a gene and is involved in recognizing and binding of RNA polymerase and other proteins, thereby directing transcription of an operably linked nucleic acid. "Promoter" herein may further include any nucleic acid sequence capable of driving transcription of a coding sequence. In particular, the term "promoter" as used herein may refer to a polynucleotide sequence generally described as the 5' regulator region of a gene, located proximal to the start codon. The transcription of one or more coding sequence is initiated at the promoter region. The term promoter may also include fragments of a promoter that are functional in initiating transcription of the gene. Promoter may also be called "transcription start site" (TSS).

Encompassed by the aforementioned terms are further transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner.

For example, enhancers as known in the art and as used herein are normally short DNA segments (e.g. 50-1500 bp) which may be bound by proteins such as transcription factors to increase the likelihood that transcription of a coding sequence will occur.

Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ. A promoter can be modified by one or more nucleotide substitution(s), insertion(s) and/or deletion(s) without interfering with functionality or activity, but it is also possible to increase the activity by modification of its sequence.

Further elements may be "transcription termination elements" which include pieces of nucleic acid sequences marking the end of a gene and mediating the transcriptional termination by providing signals within mRNA that initiates the release of the mRNA from the transcriptional complex. Transcriptional termination in prokaryotes usually is initiated by Rho-dependent or Rho-independent terminators. In eukaryotes transcription termination usually occurs through recognition of termination by proteins associated with RNA polymerase II.

An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated.

Any source of nucleic acid, in purified form can be utilized as the starting nucleic acid (also defined as "a template polynucleotide"). Thus, the process may employ DNA or RNA including messenger RNA, which DNA or RNA can be single-stranded, and preferably double stranded. In addition, a DNA-RNA hybrid which contains one strand of each may be utilized. The nucleic acid sequence may be of various lengths depending on the size of the nucleic acid sequence to be mutated. Preferably the specific nucleic acid sequence is from 50 to 50000 base pairs, and more preferably from 50-11000 base pairs.

Standard convention (5' to 3') is used herein to describe the sequence of double-stranded polynucleotides.

All methods and materials similar or equivalent to those described herein can be used in the practice or testing of methods and compositions disclosed herein, with suitable methods and materials being described herein. All publications, patent applications, patents, and other references mentioned herein are incorporated by reference in their entirety. Further, the materials, methods, and examples are illustrative only and are not intended to be limiting, unless otherwise specified.

Nuclease Polypeptides

Disclosed herein are polypeptides having nuclease activity. In some embodiments, the polypeptide is an isolated, synthetic, or recombinant polypeptide comprising an amino acid sequence having at least 80%, 85%, 90%, 95%, 98%, 99%, or more sequence identity to SEQ ID NO: 1, where the polypeptide has nuclease activity. The polypeptide can, for example, has 80%, 85%, 90%, 91%, 92%, 93%, 94%, 95%, 96%, 97%, 98%, 99%, 99.5%, or a range between any two of these values, sequence identity to SEQ ID NO: 1. As described herein, a polypeptide having the amino acid sequence of SEQ ID NO: 1 exhibits nuclease activity. The first 21 amino acids on the N-terminus of SEQ ID NO: 1 is the signal sequence, and the remaining amino acids form the mature polypeptide. The coding nucleic acid sequence of SEQ ID NO: 1 is disclosed herein as SEQ ID NO: 2. The amino acid mutations are described herein relative to the corresponding amino acid position in SEQ ID NO: 1. For example, an amino acid substitution from E to L at position 230 of SEQ ID NO: 1 is described herein as E230L.

In some embodiments, the polypeptide comprises one or more mutations of E230L, L114F, E260R, E230M, D246P, S161R, N54S, T227H, V226K, E230R, G263A, G119N, V226K, G263A, N127S, P84V, D83E, D28G, V45T, M262V, A190K, P84N, I44R, G256S, A73M, P179L, Q135E, A60P, V247I, G263K, S161E, P72N, P84L, S74N, T82R, G75R, Q141R, and D107N. In some embodiments, the polypeptide comprises one or more mutations of L114F, E230M, D107N, Q141R, G119N, S74N, T82R, and G75R. In some embodiments, the polypeptide comprises a combination of mutations selected from the group consisting of: (a) T82R, L114F, and G119N; (b) G75R, T82R, L114F, and G119N; (c) S74N, G75R, T82R, G119N, and Q141R; (d) S74N, T82R, L114F, and G119N; (e) S74N, T82R, L114F, G119N, and Q141R; (f) S74N, T82R, G119N, and Q141R; (g) S74N, L114F, and Q141R; (h) S74N, L114F, G119N, and Q141R; (i) S74N, G75R, T82R, L114F, and Q141R; (j) S74N, G75R, T82R, L114F, G119N, and Q141R; (k) S74N, G75R, T82R, and Q141R; (l) S74N, G75R, L114F, and Q141R; (m) S74N, G75R, and Q141R; (n) T82R, D107N, and G119N; (o) S74N, G75R, T82R, D107N, and Q141R; (p) S74N, G75R, G119N, and Q141R; (q) T82R, D107N, and L114F; (r) G75R, T82R, D107N, and L114F; (s) G75R, D107N, and L114F; (t) T82R, D107N, L114F, and G119N; and (u) S74N, G75R, L114F, G119N, and Q141R. In some embodiments, the polypeptide comprises a mutation or a combination of mutations selected from the group consisting of:

(T82R, L114F);
(T82R, L114F, G119N);
(T82R)
(T82R, G119N);
(L114F);
(L114F, G119N);
(G119N);
(G75R, T82R, L114F, G119N);
(G75R, T82R, L114F, G119N);
(G75R, T82R);
(G75R, L114F);
(G75R, L114F, G119N);
(S74N, G75R, T82R, G119N, Q141R);
(S74N, T82R, L114F, G119N);
(S74N, T82R, L114F, G119N, Q141R);
(S74N, T82R, Q141R);
(S74N, T82R, G119N, Q141R);
(S74N, L114F, Q141R);
(S74N, L114F, G119N, Q141R);
(S74N, Q141R);
(S74N, G75R, T82R, L114F, Q141R);
(S74N, G75R, T82R, L114F, G119N, Q141R);
(S74N, G75R, T82R, Q141R);
(S74N, G75R, L114F, Q141R);
(S74N, G75R, Q141R);
(T82R, D107N);
(G75R, T82R, D107N);
(D107N);
(G75R, T82R, G119N);
(T82R, D107N, G119N);
(G75R, T82R, D107N, G119N);
(D107N, G119N);
(G75R, D107N, G119N);
(S74N, T82R, D107N, Q141R);
(S74N, G75R, T82R, D107N, Q141R);
(S74N, G75R, D107N, Q141R);
(S74N, G119N, Q141R);
(S74N, G75R, G119N, Q141R);
(S74N, T82R, D107N, G119N, Q141R);

(S74N, G75R, T82R, D107N, G119N, Q141R);
(S74N, D107N, G119N, Q141R);
(S74N, G75R, D107N, G119N, Q141R);
(T82R, D107N, L114Ø;
(G75R, T82R, D107N, L114Ø;
(D107N, L114Ø;
(G75R, D107N, L114Ø;
(G75R, D107N);
(T82R, D107N, L114F, G119N);
(D107N, L114F, G119N);
(G75R, D107N, L114F, G119N);
(S74N, T82R, D107N, L114F, Q141R
(S74N, G75R, T82R, D107N, L114F, Q141R
(S74N, D107N, L114F, Q141R
(S74N, G75R, D107N, L114F, Q141R
(S74N, D107N, Q141R
(S74N, G75R, L114F, G119N, Q141R
(S74N, T82R, D107N, L114F, G119N, Q141R);
(S74N, G75R, T82R, D107N, L114F, G119N, Q141R);
(S74N, D107N, L114F, G119N, Q141R);
(S74N, G75R, D107N, L114F, G119N, Q141R); and
(G75R, T82R, D107N, L114F, G119N).

As used herein, a combination of amino acid mutations can be described as "Mutation1, Mutation2, and Mutation3", for example one non-limiting exemplary combination of mutations is "T82R, D107N, and G119N", or be described as (Mutation 1, Mutation 2, Mutation 3), for example one non-limiting exemplary combination of mutations is (T82R, D107N, G119N).

In some embodiments, the polypeptide is any one of the nuclease variants disclosed herein, where the polypeptide has nuclease activity.

In some embodiments, the nuclease polypeptides are thermostable, thermotolerant, or both. For example, the nuclease polypeptide can be more thermostable, thermotolerant, or both than the nuclease having the sequence of SEQ ID NO: 1 and/or its parent nuclease. In some embodiments, the nuclease activity of the polypeptide is at least 1%, 2%, 3%, 4%, 5%, 7%, 10%, 15%, 20%, 25%, 30%, 35%, 40%, 45%, 50%, or more higher than that of the nuclease having the sequence of SEQ ID NO: 1 at a given temperature, for example at a temperature between 10° C. and 70° C., or a temperature between 37° C. and 60° C., or a temperature between 40° C. and 55° C., or a temperature of 37° C. In some embodiments, the nuclease activity of the polypeptide is 1%, 2%, 3%, 4%, 5%, 7%, 10%, 15%, 20%, 25%, 30%, 35%, 40%, 45%, 50%, 75%, 100%, or a range between two of these values, higher than that of the nuclease having the sequence of SEQ ID NO: 1 at a given temperature, for example at a temperature between 10° C. and 70° C., at a temperature between 37° C. and 60° C., or temperature between 40° C. and 55° C., or a temperature of 37° C. In some embodiments, the nuclease activity of the polypeptide is at least 1%, 2%, 3%, 4%, 5%, 7%, 10%, 15%, 20%, 25%, 30%, 35%, 40%, 45%, 50%, or more higher than that of the nuclease having the sequence of SEQ ID NO: 1 at a given pH, for example at pH 4 to pH 11, or at pH 6 to pH 7.5, or at pH 6 to pH 7, or at pH 6.5 to pH 7, or at pH 6.5.

In some embodiments, the nuclease activity ratio 54° C./37° C. of the polypeptide is at least 1%, 2%, 3%, 4%, 5%, 7%, 10%, 15%, 20%, 25%, 30%, 35%, 40%, 45%, 50%, or more higher than that of the nuclease having the sequence of SEQ ID NO: 1. In some embodiments, the nuclease activity ratio 54° C./37° C. of the polypeptide is 1%, 2%, 3%, 4%, 5%, 7%, 10%, 15%, 20%, 25%, 30%, 35%, 40%, 45%, 50%, 75%, 100%, or a range between two of these values, higher than that of the nuclease having the sequence of SEQ ID NO: 1.

The optimal temperature of the polypeptide can be different (for example higher or lower) than that of the nuclease having the sequence of SEQ ID NO: 1 or its parent nuclease. For example, the optimal temperature of the polypeptide can be 1° C., 2° C., 3° C., 4° C., 5° C., 6° C., 7° C., 8° C., 9° C., 10° C., 11° C., 12° C., 13° C., 14° C., 15° C., 20° C., 25° C., or a range between any two of these values, higher than the optimal temperature of the nuclease having the sequence of SEQ ID NO: 1 or its parent nuclease. In some embodiments, the optimal temperature of the polypeptide is at least 1° C., 2° C., 3° C., 4° C., 5° C., 6° C., 7° C., 8° C., 9° C., 10° C., 11° C., 12° C., 13° C., 14° C., 15° C., 20° C., 25° C., or more, higher than the optimal temperature of the nuclease having the sequence of SEQ ID NO: 1 or its parent nuclease. In some embodiments, the optimal temperature of the polypeptide is, or is about, 10° C., 15° C., 20° C., 25° C., 30° C., 35° C., 40° C., 45° C., 50° C., 55° C., 60° C., 65° C., 70° C., 75° C., or a range between any two of these values. In some embodiments, the optimal temperature of the polypeptide is between 10° C. and 70° C. In some embodiments, the optimal temperature of the polypeptide is between 37° C. and 60° C.

The optimal pH of the polypeptide can be different (for example lower or higher) than that of the nuclease having the sequence of SEQ ID NO: 1 and/or its parent nuclease. For example, the difference between the optimal pH of the polypeptide and the optimal pH of the nuclease having the sequence of SEQ ID NO: 1 and/or its parent nuclease can be pH 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.5, 3, or more, or a range between any two of these values. In some embodiments, the optimal pH of the polypeptide is higher than the optimal pH of the nuclease having the sequence of SEQ ID NO: 1 and/or its parent nuclease. In some embodiments, the optimal pH of the polypeptide is lower than the optimal pH of the nuclease of SEQ ID NO: 1 and/or its parent nuclease. In some embodiments, the difference between the optimal pH of the polypeptide and the optimal pH of the nuclease having the sequence of SEQ ID NO: 1 and/or its parent nuclease is at least, or at most, pH 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.5, or 3. The optimal pH of the polypeptide can be, for example, 4, 4.5, 5, 5.5, 6, 6.1, 6.2, 6.3, 6.4, 6.5, 6.6, 6.7, 6.8, 6.9, 7, 7.5, 8, 8.5, 9, 9.5, 10, 10.4, or 11, or a range between any two of these values. The optimal pH of the polypeptide can be at least, or be at most, pH 4, 4.5, 5, 5.5, 6, 6.1, 6.2, 6.3, 6.4, 6.5, 6.6, 6.7, 6.8, 6.9, 7, 7.5, 8, 8.5, 9, 9.5, 10, 10.4, or 11. In some embodiments, the optimal pH of the polypeptide is between pH 4 to pH 11, pH 6 to pH 7, for example pH 6.5.

During the fermentation process, DNA from a production host can complicate many aspects of the protein recovery process. Currently, DNAse has been added in order to remove the DNA from final product, which often requires addition of costly materials from other sources. The nucleases disclosed herein can be expressed, in some embodiments, in the same production host as product of interest, which eliminates the needs to add external DNAse so that can reduce the overall cost of processing to final product.

The nuclease polypeptides disclosed herein can have one or more signal sequences. In some embodiments, at least one of the one or more signal sequences is heterologous to the nuclease polypeptide it is comprised in. In some embodiments, the nuclease polypeptides disclosed herein do not contain any signal sequences.

Also disclosed herein are antibody or binding fragment thereof (e.g., isolated or purified antibody or binding fragment thereof) which specifically binds to an isolated, synthetic, or recombinant polypeptide comprising an amino acid sequence having at least 80%, 85%, 90%, 95%, 98%, 99%, or more sequence identity to SEQ ID NO: 1, where the polypeptide has nuclease activity. The polypeptide can, for example, has 80%, 85%, 90%, 91%, 92%, 93%, 94%, 95%, 96%, 97%, 98%, 99%, 99.5%, or a range between any two of these values, sequence identity to SEQ ID NO: 1. In some embodiments, the polypeptide comprises one or more mutations of E230L, L114F, E260R, E230M, D246P, S161R, N54S, T227H, V226K, E230R, G263A, G119N, G263A, N127S, P84V, D83E, D28G, V45T, M262V, A190K, P84N, I44R, G256S, A73M, P179L, Q135E, A60P, V247I, G263K, S161E, P72N, P84L, S74N, T82R, G75R, G119N, Q141R, and D107N. In some embodiments, the polypeptide comprises a mutation of L114F, E230M, D107N, Q141R, G119N, S74N, T82R, or G75R. In some embodiments, the polypeptide comprises a combination of mutations selected from the group consisting of: (a) T82R, L114F, and G119N; (b) G75R, T82R, L114F, and G119N; (c) S74N, G75R, T82R, G119N, and Q141R; (d) S74N, T82R, L114F, and G119N; (e) S74N, T82R, L114F, G119N, and Q141R; (f) S74N, T82R, G119N, and Q141R; (g) S74N, L114F, and Q141R; (h) S74N, L114F, G119N, and Q141R; (i) S74N, G75R, T82R, L114F, and Q141R; (j) S74N, G75R, T82R, L114F, G119N, and Q141R; (k) S74N, G75R, T82R, and Q141R; (l) S74N, G75R, L114F, and Q141R; (m) S74N, G75R, and Q141R; (n) T82R, D107N, and G119N; (o) S74N, G75R, T82R, D107N, and Q141R; (p) S74N, G75R, G119N, and Q141R; (q) T82R, D107N, and L114F; (r) G75R, T82R, D107N, and L114F; (s) G75R, D107N, and L114F; (t) T82R, D107N, L114F, and G119N; and (u) S74N, G75R, L114F, G119N, and Q141R.

Variants of the nucleases disclosed herein can comprise one or more of substitutions, deletions, and insertions at one or more of the amino acid positions of the nucleases. In some embodiments, the number of amino acid substitutions, deletions and/or insertions introduced into the parent nuclease (for example the nuclease having the sequence of SEQ ID NO: 1) is not more than 30, for example, 1, 2, 3, 4, 5, 6, 7, 8, 9, 10, 11, 12, 13, 14, 15, 16, 17, 18, 19, 20, 21, 22, 23, 24, 25, 26, 27, 28, or 29. The amino acid changes can be of a minor nature, that is conservative amino acid substitutions or insertions that do not significantly affect the folding and/or activity of the protein; small deletions (for example 1-20 amino acids); small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain. In some embodiments, the amino acid changes to the nucleases can alter one or more physico-chemical properties of the parent nucleases. For example, the amino acid changes may alter (e.g., improve or decrease) one or more of the properties of the nuclease polypeptides, including but not limited to, thermal stability, substrate specificity, pH optimum, temperature optimum, and the like as compared to the parent nuclease(s).

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Non-limiting exemplary amino acid substitutions include Ala to Ser, Val to Ile, Asp to Glu, Thr to Ser, Ala to Gly, Ala to Thr, Ser to Asn, Ala to Val, Ser to Gly, Tyr to Phe, Ala to Pro, Lys to Arg, Asp to Asn, Leu to Ile, Leu to Val, Ala to Glu, and Asp to Gly.

Amino acid substitutions, deletions, and/or insertions can be made and tested using methods known in the art for protein/DNA engineering, including but not limited to mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127). In some embodiments, mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide.

In some embodiments, the nuclease polypeptides can tolerate higher or lower pH than other nucleases, for example the nuclease having the sequence of SEQ ID NO: 1. For example, the nuclease polypeptides can retain a nuclease activity (for example, at least 40%, 50%, 60%, 70%, 80%, 90%, 95%, or 98% of its nuclease activity) at, or at about, pH 3.0, pH 3.5, pH 4.0, pH 4.5, pH 5.0, pH 5.5, pH 6.0, pH 6.5, pH 7.0, pH 7.5, pH 8.0, pH 8.5, pH 9.0, pH 9.5, pH 10.0, pH 10.5, pH 11.0, pH 11.5, pH 12.0, or a range between any two of these values. For example, the nuclease polypeptides retain a nuclease activity (for example, at least 40%, 50%, 60%, 70%, 80%, 90%, 95%, or 98% of its nuclease activity) above, or below, pH 3.0, pH 3.5, pH 4.0, pH 4.5, pH 5.0, pH 5.5, pH 6.0, pH 6.5, pH 7.0, pH 7.5, pH 8.0, pH 8.5, pH 9.0, pH 9.5, pH 10.0, pH 10.5, pH 11.0, pH 11.5, pH 12.0, or a range between any two of these values. In some embodiments, these pH tolerant nuclease polypeptides are also thermostable. For example, the thermostable nuclease polypeptides can retain a nuclease activity (for example, at least 40%, 50%, 60%, 70%, 80%, 90%, 95%, or 98% of its nuclease activity) at a temperature at 10° C., 15° C., 15° C., 20° C., 25° C., 30° C., 35° C., 40° C., 41° C., 42° C., 43° C., 44° C., 45° C., 46° C., 47° C., 48° C., 49° C., 50° C., 51° C., 52° C., 53° C., 54° C., 55° C., 56° C., 56° C., 57° C., 58° C., 59° C., 60° C., 61° C., 62° C., 63° C., 64° C., 65° C., 70° C., or a range between any two of these values.

The nuclease polypeptides disclosed herein can have the same or different substrate specificity as compared to the nuclease having the sequence of SEQ ID NO: 1 or its respective parent nuclease. For example, the nuclease polypeptides can have substantially the same substrate specificity as compared to the nuclease having the sequence of SEQ ID NO: 1 or its respective parent nuclease. In some embodiments, the nuclease polypeptides have about 50%, 60%, 70%, 80%, 90%, 95%, 98%, or a range between any two of these values, substrate specificity as compared to the nuclease having the sequence of SEQ ID NO: 1 or its respective parent nuclease. Also disclosed herein is a composition that comprises one or more of the nuclease polypeptides disclosed herein.

Also provided herein are immobilized nuclease polypeptides, wherein the immobilized polypeptide comprises one of the nuclease polypeptides disclosed herein. In some embodiments, the polypeptide can be immobilized on a cell, a metal, a resin, a polymer, a ceramic, a glass, a microelectrode, a graphitic particle, a bead, a gel, a plate, an array, a capillary tube, or a combination thereof.

Production of Nuclease Polypeptides and Variants Thereof

Provided herein are methods for modifying and making variants of nuclease polynucleotides disclosed herein. Some embodiments provide synthetic or recombinant nucleic acid that encodes one or more of the polypeptides disclosed herein, and vectors (for example expression vectors) comprising the nucleic acid. Non-limiting examples of the method include synthetic ligation reassembly, random mutagenesis, targeted mutagenesis, optimized directed evolution system and/or saturation mutagenesis such as gene site saturation mutagenesis (GSSM), and any combination thereof. As used herein, the terms "saturation mutagenesis," "Gene Site Saturation Mutagenesis" and "GSSM" are used interchangeably and refers to a method that uses degenerate oligonucleotide primers to introduce point mutations into a polynucleotide. The term "optimized directed evolution system" or "optimized directed evolution" includes a method for reassembling fragments of related nucleic acid sequences, such as related genes, and explained in detail, below. The term "synthetic ligation reassembly" or "SLR" includes a method of ligating oligonucleotide fragments in a non-stochastic fashion, and explained in detail, below. The term "variant" refers to polynucleotides or polypeptides in accordance with the description modified at one or more base pairs, codons, introns, exons, or amino acid residues (respectively) yet still retain the biological activity of a nuclease. Variants can be produced by methods such as by error-prone PCR, shuffling, site-directed mutagenesis, assembly PCR, sexual PCR mutagenesis, in vivo mutagenesis (phage-assisted continuous evolution, in vivo continuous evolution), cassette mutagenesis, recursive ensemble mutagenesis, exponential ensemble mutagenesis, site-specific mutagenesis, gene reassembly, gene site saturation mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

In addition, as described in U.S. Pat. No. 9,476,078 (the content of which is hereby expressly incorporated by reference in its entirety), the tailored multi-sire combinatorial assembly ("TMCA") method can generate a specific gene variant comprising multiple changes or a combinatorial gene library efficiently and quickly; requires minimum cost and effort; and can be tailored to make biased combinatorial library according to the "needs." The TMCA method can be performed without employing a ligation step and, therefore, simplifies the process of generating multiple mutations. The "needs" of a particular library vary by experiments. Potential mutation sites—the "needs"—for example, may be either 1)

rationally designed amino acid changes or 2) individual amino acids alterations empirically determined to produce a desired effect on an enzyme (determined by GSSM and screening efforts). Each library is created with a specific number of potential mutation sites. It may be preferable to create a library biased towards progeny with either more or less mutations at the potential mutation sites. Likewise, it may be preferable to create a library in which a bias exists towards or against a particular mutation or mutation site. Various nuclease polypeptides disclosed herein were generated using the TMCA method.

Cloning vehicles comprising an expression cassette (such as a vector) can be used herein to express one or more of the nuclease polypeptides disclosed herein. The term "vector" as used herein encompasses any kind of cloning vehicles, such as but not limited to plasmids, phagemids, viral vectors (e.g., phages), bacteriophage, baculoviruses, cosmids, fosmids, artificial chromosomes, or and any other vectors specific for specific hosts of interest. Low copy number or high copy number vectors are also included. Foreign polynucleotide sequences usually comprise a coding sequence which may be referred to herein as "gene of interest". The gene of interest may comprise introns and exons, depending on the kind of origin or destination of host cell. The cloning vehicle can be a viral vector, a plasmid, a phage, a phagemid, a cosmid, a fosmid, a bacteriophage, an artificial chromosome, or a combination thereof. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC). In some embodiments, the polynucleotide sequence encoding one or more nuclease polypeptides is integrated into a chromosome of the host cell in which the polynucleotide sequence is present, and thus the polynucleotide is a part of a chromosomal of the host cell. The host cell can be, for example, a bacterial cell, a mammalian cell, a fungal cell, a yeast cell, an insect cell, or a plant cell. In some embodiments, the polynucleotide sequence encoding one or more nuclease polypeptides is not located in the chromosome of the host cell.

Also provided herein are transformed host cells comprising nucleic acids or expression cassettes (such as vectors) or cloning vehicles comprising a nucleic acid sequence that encodes one or more of the nuclease polypeptides disclosed herein. Some embodiments provide a method for producing a recombinant polypeptide having nuclease activity, where the method comprises expressing a polynucleotide encoding one or more nuclease polypeptides disclosed herein under conditions that allow expression of at least one of the one or more nuclease polypeptides, thereby producing the recombinant polypeptide having nuclease activity. In some embodiments, the polynucleotide encoding one or more nuclease polypeptides disclosed herein is operably linked to a promoter. In some embodiments, the polypeptide is present in an expression vector. In some embodiments, the polynucleotide is present in the host cell to allow expression of the polypeptide. In some embodiments, the polynucleotide is present in a chromosome of the host cell to allow expression of the polypeptide. In some embodiments, the transformed host cell is a bacterial cell, a mammalian cell, a fungal cell, a yeast cell, an insect cell or a plant cell. In some embodiments, the transformed host cell is a cell from *Pichia pastoris* (*Komagataella pastoris*), *Bacillus subtilis*, *Pseudomonas fluorescens*, *Myceliopthora thermophile* fungus, *Tricodermea reesei*, *Escherichia coli*, *Bacillus licheniformis*, *Aspergillus niger*, *Schizosaccharomyces pombe*, or. *Sacaramyces cerevisiae*

Non-limiting examples of expression vectors include viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), PI-based artificial chromosomes, yeast plasmids, yeast artificial chromosomes, and any other vectors specific for specific hosts of interest (such as *bacillus*, *aspergillus* and yeast). Nuclease-encoding DNA disclosed herein can be included in any one of a variety of expression vectors for expressing a nuclease polypeptide. Such vectors include chromosomal, nonchromosomal and synthetic DNA sequences. Many suitable vectors are known to those of skill in the art, and are commercially available, for example, bacterial: pQE vectors (Qiagen), pBluescript plasmids, pNH vectors, (lambda-ZAP vectors (Stratagene); ptrc99a, pKK223-3, pDR540, pRIT2T (Pharmacia); and eukaryotic: pXT1, pSG5 (Stratagene), pSVK3, pBPV, pMSG, pSVLSV40 (Pharmacia). Depending on the desired use, low copy number or high copy number vectors can be used.

Codon optimization can be used to achieve high levels of protein expression in host cells. In some embodiments, codons in a nucleic acid encoding one or more of the nuclease polypeptides disclosed herein can be optimized to increase or decrease its expression in a host cell. For example, one or more of non-preferred or less preferred codons in the nucleic acid encoding the nuclease polypeptides can be replaced with one or more "preferred codons" encoding the same amino acid for a host cell of interest. As used herein, a "preferred codon" is a codon over-represented in coding sequences in genes in a host cell, and a "non-preferred or less preferred codon" is a codon under-represented in coding sequences in genes in the host cell.

Host cells for expressing the nucleic acids, expression cassettes and vectors in accordance with the present disclosure could be a eukaryotic cell or a prokaryotic cell, and could include bacteria, yeast, fungi, plant cells, insect cells and mammalian cells; and provides methods for optimizing codon usage in all of these cells, codon-altered nucleic acids and polypeptides made by the codon-altered nucleic acids. Exemplary host cells include gram negative bacteria, such as *Escherichia coli*; gram positive bacteria, such as *Streptomyces* sp., *Lactobacillus gasseri*, *Lactococcus lactis*, *Lactococcus cremoris*, *Bacillus subtilis*, and *Bacillus cereus*. Exemplary host cells also include eukaryotic organisms, such as various yeast, such as *Saccharomyces* sp., including *Saccharomyces cerevisiae*, *Schizosaccharomyces pombe*, *Pichia pastoris*, and *Kluyveromyces lactis*, *Hansenula polymorpha*, *Aspergillus niger*, and mammalian cells and cell lines and insect cells and cell lines. In some embodiments, the host cell is a cell from an organism selected from the group consisting of *Pichia pastoris* (*Komagataella pastoris*), *Bacillus subtilis*, *Pseudomonas fluorescens*, *Myceliopthora thermophile* fungus, *Tricodermea reesei*, *Escherichia coli*, *Bacillus licheniformis*, *Aspergillus niger*, *Schizosaccharomyces pombe*, and s. *Sacaramyces cerevisiae*. The nucleic acid encoding the nuclease polypeptide disclosed herein can be located on the genome of the host cell, for example be a part of a chromosome of the host cell. In some embodiments, the nucleic acid encoding the nuclease polypeptide is located on an expression vector separate from the genome of the host cell. Methods of producing a nuclease polypeptide disclosed herein can, in some embodiments, comprise, expressing a nucleic acid encoding the nuclease polypeptide under conditions that allow expression of the nuclease polypeptide, thereby producing the nuclease polypeptide. In some embodiments, the nucleic acid encoding the nuclease polypeptide is operably linked to an inducible promoter, for example a promoter inducible by changes in temperature and/or pH, and/or by the presence, absence or change in amount/concentration of a compound (e.g., Isopropyl β-D-1-thiogalactopyranoside (IPTG), arabinose, tetracycline, steroids, and metal).

The description also includes nucleic acids and polypeptides optimized for expression in these organisms and species.

Use of Nuclease Polypeptides

Some embodiments provide methods for degrading a polynucleotide using one or more of the nuclease polypeptides disclosed herein. In some embodiments, the method comprises contacting one or more polynucleotide molecules with one or more of the nuclease polypeptides disclosed herein, thereby degrading the polynucleotide molecules. The polynucleotide molecules can comprise DNA (e.g., single- or double-stranded DNA), RNA (e.g., single- or double-stranded DNA), or any combination thereof. The contacting can occur at various pH values, for example pH 4, pH 5, pH 6, pH 7, pH 8, pH 9, pH 10, pH 11, or a range between any two of these values. The contacting can also occur at various temperatures, for example, 10° C., 15° C., 20° C., 25° C., 30° C., 35° C., 40° C., 45° C., 50° C., 55° C., 60° C., 65° C., 70° C., or a range between any two of these values. The one or more polynucleotide molecules can be comprised in various objects, for example a composition for washing (e.g., textile, clothing, cotton, fabric, or any combination thereof), or an aqueous solution (e.g., a reaction mixture).

Nucleases have been used in a wide range of applications, for example pharmaceutical, agricultural and industrial applications. Provided herein are compositions and kits that comprise one or more nuclease polypeptides disclosed herein. The composition can be an enzyme composition, a detergent composition, a detergent additive, a food, a food supplement, a feed supplement, a feed, a pharmaceutical composition, a fermentation product, a fermentation intermediate, a fermentation downstream reaction mixture, a reaction mixture, or a combination thereof. In some embodiments, the reaction mixture is for protein expression or purification. The enzyme composition can, for example, comprise one or more of the nuclease polypeptide disclosed herein and a storage buffer. In some embodiments, the storage buffer comprises a pH buffering system (e.g., Tris-HCl) providing a pH of about 6.0-9.0, for example pH 6.0-7.0 or about pH 6.5. The storage buffer can, for example, include a stabilizing agent such as glycerol. In some embodiments, the storage buffer includes glycerol at a concentration of at least about 5%, 10%, 20%, 30%, 40%, 50%, or more. In some embodiments, the storage buffer includes glycerol at a concentration of about 30-70%, for example 40-60%.

Also disclosed herein is a method for degrading polynucleotides during expression or production of a protein of interest. The method, in some embodiments, comprises culturing a host cell, wherein the host cell comprises a nucleic acid encoding a protein of interest; and expressing one or more of the nuclease polypeptides disclosed herein under conditions that allow degradation of polynucleotides by at least one of the one or more nuclease polypeptides. The polynucleotide molecules can comprise DNA, RNA, or any combination thereof. The polynucleotide molecules can comprise DNAs or RNAs (or fragments thereof) from the host cell. In some embodiments, the protein of interest is not a nuclease. In some embodiments, the protein of interest is not any one of the one or more nuclease polypeptides. The one or more nuclease polypeptides can be expressed from, for example, one or more expression vectors present in the host cell, or a nucleic acid sequence in a chromosome of the host cell. In some embodiments, at least one of the one or more nuclease polypeptides is not expressed by cells that express the protein of interest. In some embodiments, the one or more nuclease polypeptides are expressed by cells that do not express the protein of interest. The expression of the protein of interest and/or the expression of the nuclease polypeptide can be inducible. For example, the coding sequence of the protein of interest, the coding sequence of the nuclease polypeptide, or both, can be operably linked with an inducible promoter. The inducible promoter can be, for example, induced by the presence, absence, and/or change in amount of one or more chemical or biological compounds, change in pH, temperature, osmolarity, ionic strength/concentration, or any combination thereof. Some embodiments provide a host cell comprising a nucleic acid encoding a protein of interest and a nucleic acid encoding one or more of the nuclease polypeptides disclosed herein.

The compositions can be formulated in a variety of forms, such as tablets, gels, pills, implants, liquids, sprays, films, micelles, powders, food, feed pellets, a type of encapsulated form, or a combination thereof.

In some embodiments, the nuclease polypeptides disclosed herein can be used alone, or in combination with one or more additional enzymes in a detergent application. Some embodiments provide detergent compositions comprising the nucleases and their variants disclosed herein. In some embodiments, the detergent composition can further comprise one or more additional enzymes, or one or more additional components, or any combination thereof. The detergent composition can be, for example, a hand or machine laundry detergent composition. The one or more additional components include but not limited to, one or more laundry additive compositions suitable for pre-treatment of stained fabrics and a rinse added fabric softener composition. The detergent composition can be formulated, for example, for use in general household hard surface cleaning operations, or for hand or machine dishwashing operations. Non-limiting examples of the additional components include surfactants (e.g., anionic surfactants, cationic surfactants, non-ionic surfactants, semi-polar surfactants, zwitterionic surfactants, or a mixture thereof), builders, co-builders, bleach systems, polymers, fabric hueing agents, anti-foaming agents, soil release polymers, anti-redeposition agents, hydrotropes, wetting agents, thickening agents, buffer(s) for pH control, stabilizers, perfume, colorants, fillers and the like, or any combination thereof. The builder and/or co-builder can be, for example, a chelating agent that forms water-soluble complexes with Ca and Mg.

Some embodiments provide methods of using the nucleases and their variants in a detergent application. For example, the method can comprise (a) contacting a textile to a detergent composition comprising one or more of the nucleases and their variants disclosed herein, and (b) performing at least one wash cycle to wash the textile. The method can, for example, further comprise rinsing the washed textile. In some embodiments, the detergent composition further comprises one or more additional enzymes. In some embodiments, the textile is an item made of cotton or a synthetic material, for example a piece of sportswear, a T-shirt, or a piece of clothing which is exposed to sweat when used. The textile can also be bedding, bed linen or towels.

As disclosed herein, the one or more additional enzymes can include, but are not limited to, one or more of nucleases, proteases, lipases, cutinases, amylases, carbohydrases, cellulases, pectinases, mannanases, arabinases, galactanases, xylanases, oxidases (e.g., laccases and peroxidases), and deoxyribonucleases (DNases). The detergent composition can, for example, be used in a washing method for textile. In some embodiments, the detergent composition can comprise one or more of the following anionic surfactants: linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SD S), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES), methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap.

Also provided are pharmaceutically acceptable prodrugs of the pharmaceutical compositions, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the agent). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in Bundgaard, *Design of Prodrugs* (Elsevier Press, 1985).

Also provided are pharmaceutically active metabolites of the pharmaceutical compositions, and uses of such metabolites in the methods of the description. A "pharmaceutically active metabolite" means a pharmacologically active product of metabolism in the body of a compound or salt thereof. Prodrugs and active metabolites of a compound may be determined using routine techniques known or available in the art. See, e.g., Bertolini et al., *J. Med. Chem.* 1997, 40, 2011-2016; Shan et al., *J Phann. Sci.* 1997, 86 (7), 765-767; Bagshawe, *Drug Dev. Res.* 1995, 34, 220-230; Bodor, *Adv. Drug Res.* 1984, 13, 255-331; Bundgaard, *Design of Prodrugs* (Elsevier Press, 1985); and Larsen, Design and *Application of Prodrugs, Drug Design and Development* (Krogsgaard-Larsen et al., eds., Harwood Academic Publishers, 1991).

Any suitable formulation of the compounds described herein can be prepared. See, generally, *Remington's Pharmaceutical Sciences*, (2000) Hoover, J. E. editor, 20th edition, Lippincott Williams and Wilkins Publishing Company, Easton, Pa., pages 780-857. A formulation is selected to be suitable for an appropriate route of administration. Some routes of administration are oral, parenteral, by inhalation, topical, rectal, nasal, buccal, vaginal, via an implanted reservoir, or other drug administration methods. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example, by a sufficiently basic compound such as an amine with a suitable acid, affording a physiologically acceptable anion. Alkali metal (e.g., sodium, potassium or lithium) or alkaline earth metal (e.g., calcium) salts of carboxylic acids also are made.

In some embodiments, the composition comprising one or more nuclease polypeptides disclosed herein is a pharmaceutical composition or an anti-biofouling composition for disrupting a biofilm, for prevention biofilm formation, or both. In some embodiments, the pharmaceutical composition is used for treating dental plaque; dental caries; periodontitis; native valve endocarditis; chronic bacterial prostatitis; otitis media; infections associated with medical devices such as artificial heart valves, artificial pacemakers, contact lenses, prosthetic joints, sutures, catheters, and arteriovenous shunts; infections associated with wounds, lacerations, sores and mucosal lesions such as ulcers; infections of the mouth, oropharynx, nasopharynx and laryngeal pharynx; infections of the outer ear; infections of the eye; infections of the stomach, small and large intestines; infections of the urethra and vagina; infections of the skin; intra-nasal infections, such as infections of the sinus; or a combination thereof. In some embodiments, the composition comprising one or more nuclease polypeptides disclosed herein is a pharmaceutical composition for oral care, treating wound, or both. In some embodiments, the method for using the composition comprises contacting the composition with a biofilm. In some embodiments, the method for using the composition comprises contacting the composition with a wound, a laceration, a sore, a mucosal lesion, or any combination thereof. In some embodiments, the method for using the composition comprises contacting the composition with a medical device. In some embodiments, the method for using the composition comprises contacting the composition with skin, outer ear, eye, or a combination thereof.

In some embodiments, the composition comprising one or more nuclease polypeptides disclosed herein is used to contact a food machinery comprising DNA substrate and to clean the food machinery. In some embodiments, the composition comprising one or more nuclease polypeptides disclosed herein is used to contact a surface comprising DNA substrate and to clean the surface. In some embodiments, the composition comprising one or more nuclease polypeptides disclosed herein is used to contact a paper machine comprising DNA substrate and to clean the paper machine.

EXAMPLES

Some aspects of the embodiments discussed above are disclosed in further detail in the following examples, which are not in any way intended to limit the scope of the present disclosure.

Protocols used for testing nuclease variants in the following examples are provided below.

PicoGreen Assay

Reagents used in the PicoGreen array included:

37° C. buffer: 50 mM Tris-HCl, pH8.30, 1 mM $MgCl_2$, with or without 0.1-1 mg/mL BSA; or 50 mM Bis-Tris Propane, pH8, 1 mM $MgCl_2$, with or without 0.1-1 mg/mL BSA;

54° C. buffer: 50 mM Tris-HCl, pH8.78, 1 mM MgCl$_2$, with or without 0.1-1 mg/mL BSA; or 50 mM Bis-Tris Propane, pH8, 1 mM MgCl$_2$, with or without 0.1-1 mg/mL BSA;

Enzyme dilution buffer: 37 C buffer with 0.1-1 mg/mL BSA;

Substrate stock: Herring Sperm DNA (Promega D1815), 10 mg/mL;

37° C. substrate: 4800 ng/mL herring sperm DNA in 37° C. buffer;

54° C. substrate: 7200 ng/mL herring sperm DNA in 54° C. buffer;

PicoGreen Dye: Thermal Fisher (P7581);

PicoGreen reagent: dilute the PicoGreen dye original stock from vendor 50 times in 50 mM Tris-HCl, pH 7.5 buffer.

Supernatant samples were diluted in enzyme dilution buffer at appropriate dilutions. For the 37° C. assay, 30 uL of 37 C substrate was mixed with 10 uL of diluted sample/control, and incubated at 37° C. for 1 hour. For the 54° C. assay, 20 uL of 54° C. substrate was mixed with 20 uL of diluted sample/control, and incubated at 54 C for 1 hour. After incubation, 30 uL of PicoGreen reagent was added. Fluorescence was read at Ex/Em=480/520 nm. PicoGreen dye would bind to non-degraded double strand DNA and exhibit fluorescence signal.

DNA degradation percentage (also referred to herein as "DNA degradation %," typically within 20-60%) was calculated as: (fluorescence of wells without enzymes-fluorescence of wells with enzymes)/fluorescence of wells without enzymes×100%. In some examples, activity ratio was calculated by DNA degradation percentage at 54° C./37° C.

A260 Assay

Reagents used in the A260 assay included:

37° C. buffer: 50 mM Tris-HCl, pH8.30, 1 mM MgCl$_2$, with or without 0.1-1 mg/mL BSA; or 50 mM Bis-Tris Propane, pH8, 1 mM MgCl$_2$, with or without 0.1-1 mg/mL BSA;

54° C. buffer: 50 mM Tris-HCl, pH8.78, 1 mM MgCl$_2$, with or without 0.1-1 mg/mL BSA; or 50 mM Bis-Tris Propane, pH8, 1 mM MgCl$_2$, with or without 0.1-1 mg/mL BSA;

Enzyme dilution buffer: 37° C. buffer with 0.1-1 mg/mL BSA;

Substrate stock: Herring Sperm DNA (Promega D1815), 10 mg/mL;

37° C. substrate: 0.4 mg/mL herring sperm DNA in 37° C. buffer;

54° C. substrate: 0.4 mg/mL herring sperm DNA in 54° C. buffer;

4% perchloric acid.

Supernatant samples were diluted in enzyme dilution buffer at appropriate dilutions. In shallow transparent 96-well plate, reaction was set up in each well. For 37° C. assay, mix 7 uL of diluted enzyme/control and 140 uL of 37° C. substrate. For 54° C. assay, mix 21 uL of diluted enzyme/control and 140 uL of 54° C. substrate. Assay plates were incubated at 37° C. and 54° C. respectively for 1 hour. After incubation, add 147 uL of 4% perchloric acid to each well and centrifuge at 3200 g at 10° C. for 15 minutes. 230 uL of supernatant was transferred from each plate to UV transparent plate, and absorbance was read at 260 nm. Degraded DNA exhibited increased Absorbance 260 signal compared to non-degraded DNA, and higher A260 values corresponded to high nuclease activities. In some examples, activity ratio was calculated by increased Abs260 at 54° C./37° C.

Fluorescence Resonance Energy Transfer (FRET) Assay—Nuclease Detection System

The FRET assay was modified from manufacture manual, IDT DNaseAlert™ Substrate. Reagents used in the assay included:

Substrate: DNaseAlert™ Substrate (IDT, cat #11-04-02-04). 1 mL nuclease-free water was added to the substrate bottle, substrate concentration=2 mM;

37° C. buffer: 50 mM Tris-HCl, pH8.30, 1 mM MgCl$_2$, with or without 0.1-1 mg/mL BSA; or 50 mM Bis-Tris Propane, pH8, 1 mM MgCl$_2$, with or without 0.1-1 mg/mL BSA;

54° C. buffer: 50 mM Tris-HCl, pH8.78, 1 mM MgCl$_2$, with or without 0.1-1 mg/mL BSA; or 50 mM Bis-Tris Propane, pH8, 1 mM MgCl$_2$, with or without 0.1-1 mg/mL BSA;

Enzyme dilution buffer: 37° C. buffer with 0.1-1 mg/mL BSA.

In 96-well half area plates, 5 uL of DNA substrate (2 uM) was mixed with 40 uL of BTP buffer and pre-heated at 37° C. or 54° C. for 10 minutes. Enzyme samples were diluted in enzyme dilution buffer around 20-40 times. 5 uL of diluted samples was added to substrate solution and read at 37° C. or 54° C. for 15 minutes, excitation=536 nm, emission=566 nm. Slope was calculated by fitting the first three points and obtained RFU/min.

It was expected that higher slope corresponded to higher nuclease activity. If the slope was too high or too low and outside of the linear range, sample dilution were adjusted and assay were performed again. In some examples, activity ratio was calculated by slope at 54° C./37° C.

Protein Quantification by LabChip and ELISA

Protein quantifications were performed by LabChip or the enzyme-linked immunosorbent assay (ELISA) according to the manufacture's protocol or standard protocol.

Protocol was slightly modified from the protocol provided by Caliper LifeSciences. LabChip GXII Protein Assay Quick Guide (Caliper LifeSciences, Hopkinton, Mass.) was followed for high sensitivity samples. Briefly, samples were prepared as below: (1) denaturing solution was prepared by adding 24.5 uL β-mercaptoethanol to 700 uL of Protein Express Sample Buffer; (2) 10 uL of protein sample was added to 14 uL denaturing solution. Samples could be prepared in 96-well plate; (3) 12 uL of Protein Express Ladder was transferred to microcentrifuge tube, but did not add denaturing solution; (4) samples and ladder were denatured at 100° C. for 5 minutes; (5) 64 uL water was added to samples and 120 uL water was added to ladder, and centrifuged at 1200 g for 2 minutes to get rid of bubbles; (6) 120 uL of ladder was transferred to the provided Ladder tube; and (7) LabChip measurement was performed according to manufacture protocol.

Protein Quantification was conducted by ELISA using standard protocol.

Example 1

Test Nuclease Variants by PicoGreen Assay

PicoGreen assay was used to select desired nuclease variants generated by GSSM (also referred to herein as "GSSM variants"). DNA degradation percentage 54° C./37° C. ratio of the nuclease variants relative to that of the parent nuclease, and expression level of the nuclease variants were used as selection criteria.

Enzyme expression level was determined by enzyme dilution before the activity assay at 37° C. Enzyme expression is denoted with "x", and the expression level is defined as shown below in Table 1.

TABLE 1

Determination of protein expression level

| Dilution Factor (DF) Range | Expression Level |
|---|---|
| DF >= 20000 | xxxx |
| 1000 < DF < 20000 | xxx |
| DF 500 =< DF <= 1000 | xx |
| DF < 500 | x |

54° C. Specific Activity Index was calculated by DNA degradation %×dilution factor at 54° C. divided by enzyme concentration. Various nuclease variants generated by GSSM were tested, and the assay results are shown in Table 2. Variants VAR002, VAR003, VAR030, VAR033, VAR035, VAR036, and VAR037 were selected since their activity at 54° C. was improved compared to the parent nuclease and they were expressed at or above a desired level.

TABLE 2

Properties of nuclease variants

| Name | DNA degradation % 54° C./37° C. | 54° C. Specific Activity Index | Sequence/ Mutation(s) | 54° C. Specific Activity compared to parent | Expression Level | DNA degradation % 54° C./37° C. relative to parent |
|---|---|---|---|---|---|---|
| Parent Nuclease | 0.128 | | SEQ ID NO: 1 | | | |
| VAR001 | 0.130 | 24672 | E230L | 102% | xxxx | 90% |
| VAR002 | 0.187 | 11348 | L114F | 47% | xxxx | 129% |
| VAR003 | 0.172 | 13973 | L114F | 58% | xxxx | 119% |
| VAR004 | 0.145 | 20003 | E260R | 83% | xxx | 100% |
| VAR005 | 0.132 | 32956 | E230M | 137% | xxx | 92% |
| VAR006 | 0.142 | 22816 | D246P | 95% | xxx | 98% |
| VAR007 | 0.140 | 34175 | S161R | 142% | xxx | 97% |
| VAR008 | 0.184 | | N54S, E230M | | xx | 127% |
| VAR009 | 0.180 | 15832 | T227H | 66% | xx | 125% |
| VAR010 | 0.191 | | V226K | | xx | 132% |
| VAR011 | 0.164 | 20000 | E230R | 83% | xx | 114% |
| VAR012 | 0.171 | | G263A | | xx | 118% |
| VAR013 | 0.139 | | V226K | | xx | 96% |
| VAR014 | 0.142 | | G263A | | xx | 98% |
| VAR015 | 0.160 | 3417 | N127S | 14% | xx | 111% |
| VAR016 | 0.165 | | P84V | | xx | 114% |
| VAR017 | 0.196 | 4514 | D83E | 19% | xx | 136% |
| VAR018 | 0.128 | | D28G, V45T | | x | 89% |
| VAR019 | 0.146 | | M262V | | x | 101% |
| VAR020 | 0.144 | | A190K | | x | 100% |
| VAR021 | 0.206 | | P84N | | x | 142% |
| VAR022 | 0.218 | | I44R | | x | 151% |
| VAR023 | 0.133 | | G256S | | x | 92% |
| VAR024 | 0.205 | | A73M, P179L | | x | 141% |
| VAR025 | 0.210 | | I44R | | x | 145% |
| VAR026 | 0.275 | | Q135E | | x | 190% |
| VAR027 | 0.307 | 84913 | A60P | 15% | xx | 239% |
| VAR028 | 0.115 | 432703 | V247I | 79% | xxx | 90% |
| VAR029 | 0.101 | 184464 | G263K | 34% | xx | 79% |
| VAR030 | 0.145 | 585026 | G119N | 107% | xxxx | 113% |
| VAR031 | 0.133 | 644722 | S161E | 118% | xxxx | 103% |
| VAR032 | 0.337 | 186139 | P72N | 34% | xx | 263% |
| VAR033 | 0.148 | 819361 | D107N | 149% | xxxx | 115% |
| VAR034 | 0.309 | 98026 | P84L | 18% | xx | 241% |
| VAR035 | 0.172 | 884237 | S74N, Q141R | 161% | xxxx | 134% |
| VAR036 | 0.141 | 1165338 | T82R | 213% | xxxx | 110% |
| VAR037 | 0.161 | 1096140 | G75R | 200% | xxxx | 126% |
| VAR038 | 0.146 | 1024096 | G75R | 187% | xxxx | 114% |

Example 2

Test Nuclease Variants Generated by TMSCA

FRET assay was used to select desired nuclease variants generated by TMSCA (also referred to herein as "TMSCA mutants"). 54° C./37° C. reaction rate ratio (>1) and enzyme dilution factor (>20) were used as selection criteria. Selected variants had improved activity at 54° C. compared to the parent nuclease. The results of the FRET assay are shown in Table 3.

TABLE 3

Properties of nuclease variants generated by TMSCA

| Name | Sequence/Mutations | 54° C./37° C. Reaction Speed Ratio |
|---|---|---|
| Parent nuclease | SEQ ID NO: 1 | 0.62 |
| VAR045 | T82R, L114F | 1.00 |
| VAR046 | T82R, L114F, G119N | 1.11 |
| VAR047 | T82R | 0.56 |

TABLE 3-continued

Properties of nuclease variants generated by TMSCA

| Name | Sequence/Mutations | 54° C./37° C. Reaction Speed Ratio |
|---|---|---|
| VAR048 | T82R, G119N | 0.64 |
| VAR049 | L114F | 0.76 |
| VAR050 | L114F, G119N | 0.75 |
| VAR051 | G119N | 0.70 |
| VAR052 | G75R, T82R, L114F | 1.25 |
| VAR053 | G75R, T82R, L114F, G119N | 1.62 |
| VAR054 | G75R, T82R | 0.75 |
| VAR055 | G75R, L114F | 0.83 |
| VAR056 | G75R, L114F, G119N | 1.14 |
| VAR057 | G75R | 0.68 |
| VAR058 | G75R, G119N | 0.65 |
| VAR060 | S74N, G75R, T82R, G119N, Q141R | 3.37 |
| VAR061 | S74N, T82R, L114F, Q141R | 2.06 |
| VAR062 | S74N, T82R, L114F, G119N, Q141R | 1.98 |
| VAR063 | S74N, T82R, Q141R | 1.24 |
| VAR064 | S74N, T82R, G119N, Q141R | 1.39 |
| VAR065 | S74N, L114F, Q141R | 1.21 |
| VAR066 | S74N, L114F, G119N, Q141R | 1.27 |
| VAR067 | S74N, Q141R | 0.80 |
| VAR068 | S74N, G75R, T82R, L114F, Q141R | 3.55 |
| VAR069 | S74N, G75R, T82R, L114F, G119N, Q141R | 2.70 |
| VAR070 | S74N, G75R, T82R, Q141R | 2.90 |
| VAR071 | S74N, G75R, L114F, Q141R | 3.27 |
| VAR072 | S74N, G75R, Q141R | 2.87 |
| VAR073 | T82R, D107N | 1.57 |
| VAR074 | G75R, T82R, D107N, | 1.48 |
| VAR075 | D107N | 0.39 |
| VAR076 | G75R, T82R, G119N | 0.97 |
| VAR077 | T82R, D107N, G119N | 1.44 |
| VAR078 | G75R, T82R, D107N, G119N | 1.16 |
| VAR079 | D107N, G119N | 1.72 |
| VAR080 | G75R, D107N, G119N | 1.28 |
| VAR081 | S74N, T82R, D107N, Q141R | 1.64 |
| VAR082 | S74N, G75R, T82R, D107N, Q141R | 1.96 |
| VAR083 | S74N, G75R, D107N, Q141R | 1.78 |
| VAR084 | S74N, G119N, Q141R | 1.19 |
| VAR085 | S74N, G75R, G119N, Q141R | 2.77 |
| VAR086 | S74N, T82R, D107N, G119N, Q141R | 1.64 |
| VAR087 | S74N, G75R, T82R, D107N, G119N, Q141R | 2.19 |
| VAR088 | S74N, D107N, G119N, Q141R | 1.69 |
| VAR089 | S74N, G75R, D107N, G119N, Q141R | 1.49 |
| VAR090 | T82R, D107N, L114F | 1.87 |
| VAR091 | G75R, T82R, D107N, L114F | 1.75 |
| VAR092 | D107N, L114F | 1.60 |
| VAR093 | G75R, D107N, L114F | 1.47 |
| VAR094 | G75R, D107N | 1.59 |
| VAR095 | T82R, D107N, L114F, G119N | 1.57 |
| VAR096 | D107N, L114F, G119N | 1.59 |
| VAR097 | G75R, D107N, L114F, G119N | 1.57 |
| VAR098 | S74N, T82R, D107N, L114F, Q141R | 1.95 |
| VAR099 | S74N, G75R, T82R, D107N, L114F, Q141R | 1.95 |
| VAR100 | S74N, D107N, L114F, Q141R | 2.03 |
| VAR101 | S74N, G75R, D107N, L114F, Q141R | 1.43 |
| VAR102 | S74N, D107N, Q141R | 1.45 |
| VAR103 | S74N, G75R, L114F, G119N, Q141R | 2.76 |
| VAR104 | S74N, T82R, D107N, L114F, G119N, Q141R | 2.04 |
| VAR105 | S74N, G75R, T82R, D107N, L114F, G119N, Q141R | 1.82 |
| VAR106 | S74N, D107N, L114F, G119N, Q141R | 4.95 |

Example 3

Test Nuclease Variants by A260 Assay

A number of nuclease variants generated by TMSCA were tested using A260 assay. The results of the assay are shown in Table 4. The selection criteria used were: activity 54° C./37° C. at pH7 and pH8 both >1; at 37° C., pH7/pH8>0.9; and at 54° C., pH7/pH8>0.5. Selected hits have improved activity than the parent at pH7 and pH8, at 54° C.; at 37° C. and 54° C., activity at pH7.

TABLE 4

A260 assay results of TMSCA nuclease variants

| | pH 8 54° C./37° C. | pH 7 54° C./37° C. | 37° C. pH 7/pH 8 | 54° C. pH 7/pH 8 |
|---|---|---|---|---|
| VAR046 | 0.78 | 0.23 | 0.81 | 0.24 |
| VAR053 | 1.04 | 0.62 | 0.95 | 0.57 |
| VAR060 | 2.56 | 1.87 | 1.08 | 0.79 |
| VAR061 | 2.70 | 1.29 | 1.07 | 0.51 |
| VAR062 | 2.40 | 1.28 | 1.07 | 0.57 |
| VAR064 | 1.25 | 0.86 | 0.90 | 0.62 |
| VAR065 | 1.10 | 0.44 | 1.08 | 0.43 |
| VAR066 | 2.34 | 0.70 | 1.08 | 0.33 |
| VAR068 | 2.91 | 2.12 | 1.12 | 0.82 |
| VAR069 | 3.48 | 2.75 | 1.12 | 0.88 |
| VAR070 | 2.80 | 2.05 | 1.17 | 0.86 |
| VAR071 | 3.02 | 2.05 | 1.18 | 0.80 |
| VAR072 | 2.51 | 1.51 | 1.06 | 0.63 |
| VAR077 | 0.56 | 0.42 | 0.16 | 0.12 |
| VAR078 | 2.14 | 1.30 | 0.69 | 0.42 |
| VAR085 | 1.63 | 1.04 | 1.09 | 0.70 |
| VAR090 | 0.48 | 0.58 | 0.22 | 0.27 |
| VAR091 | 1.36 | 0.97 | 0.30 | 0.21 |
| VAR093 | 0.73 | 0.94 | 0.36 | 0.46 |
| VAR095 | 0.54 | 0.74 | 0.21 | 0.28 |
| VAR103 | 3.46 | 2.78 | 1.01 | 0.81 |
| Seq 1 | 0.23 | 0.14 | 0.43 | 0.27 |

Example 4

Temperature Profiling of Nuclease Variants Generated by TMSCA

A number of nuclease variants generated by TMSCA were tested for temperature profiling. The test results are shown in Table 5 (PC=positive control, and NC=negative control) and FIG. 2. In Table 5, the temperature ("temp") under which the nuclease variants were tested is provided at the most left column.

TABLE 5

A260 assay results normalized by maximum activity % for TMSCA nuclease variants

| Temp | VAR060 | VAR061 | VAR062 | VAR068 | VAR069 | VAR070 | VAR071 | VAR072 | VAR085 | VAR103 | POS | NC |
|---|---|---|---|---|---|---|---|---|---|---|---|---|
| 70 | 15 | 13 | 11 | 29 | 28.3 | 15.9 | 17.6 | 11.0 | 11.8 | 16.0 | 10.3 | |
| 68.7 | 18 | 15 | 13 | 32 | 33.3 | 18.8 | 22.0 | 130 | 141 | 198 | 10.0 | |

TABLE 5-continued

A260 assay results normalized by maximum activity % for TMSCA nuclease variants

| Temp | VAR060 | VAR061 | VAR062 | VAR068 | VAR069 | VAR070 | VAR071 | VAR072 | VAR085 | VAR103 | POS | NC |
|---|---|---|---|---|---|---|---|---|---|---|---|---|
| 65.9 | 32 | 25 | 24 | 41 | 42.4 | 29.9 | 33.2 | 224 | 239 | 297 | 10.1 | |
| 61.8 | 52 | 43 | 50 | 56 | 60.7 | 49.9 | 50.8 | 460 | 452 | 451 | 10.8 | |
| 57 | 83 | 59 | 72 | 84 | 92.9 | 71.5 | 67.8 | 688 | 677 | 740 | 14.0 | |
| 53 | 96 | 85 | 95 | 98 | 99.6 | 94.3 | 96.7 | 926 | 974 | 973 | 21.4 | |
| 50.3 | 100.0 | 100.0 | 100.0 | 100.0 | 100.0 | 100.0 | 100.0 | 100.0 | 100.0 | 100.0 | 31.0 | |
| 49 | 91 | 100 | 94 | 90 | 86.2 | 93.1 | 92.6 | 89.4 | 96.5 | 90.2 | 43.6 | |
| 47.7 | 83 | 98 | 86 | 83 | 76.6 | 85.5 | 85.0 | 80.2 | 85.5 | 78.8 | 55.8 | |
| 45.3 | 74 | 95 | 74 | 73 | 63.4 | 79.2 | 74.2 | 73.3 | 77.4 | 66.8 | 71.8 | |
| 41.5 | 53 | 76 | 52 | 48 | 40.1 | 59.6 | 48.6 | 50.5 | 55.9 | 43.7 | 91.1 | |
| 37.2 | 37 | 54 | 36 | 31 | 25.8 | 43.7 | 30.9 | 36.3 | 39.4 | 26.9 | 98.5 | |
| 33.6 | 29.0 | 40.0 | 27.0 | 21.0 | 18.3 | 33.5 | 20.5 | 27.4 | 30.0 | 17.8 | 99.2 | |
| 31.2 | 23.0 | 33.0 | 22.0 | 16.0 | 14.3 | 26.3 | 15.1 | 22.2 | 24.7 | 13.7 | 100.0 | |
| 30 | 21.0 | 29.0 | 20.0 | 14.0 | 12.1 | 23.9 | 12.6 | 19.2 | 21.4 | 11.6 | 97.7 | |

Example 5 pH Profiling of Nuclease Variants at 37° C.

Figure 3:
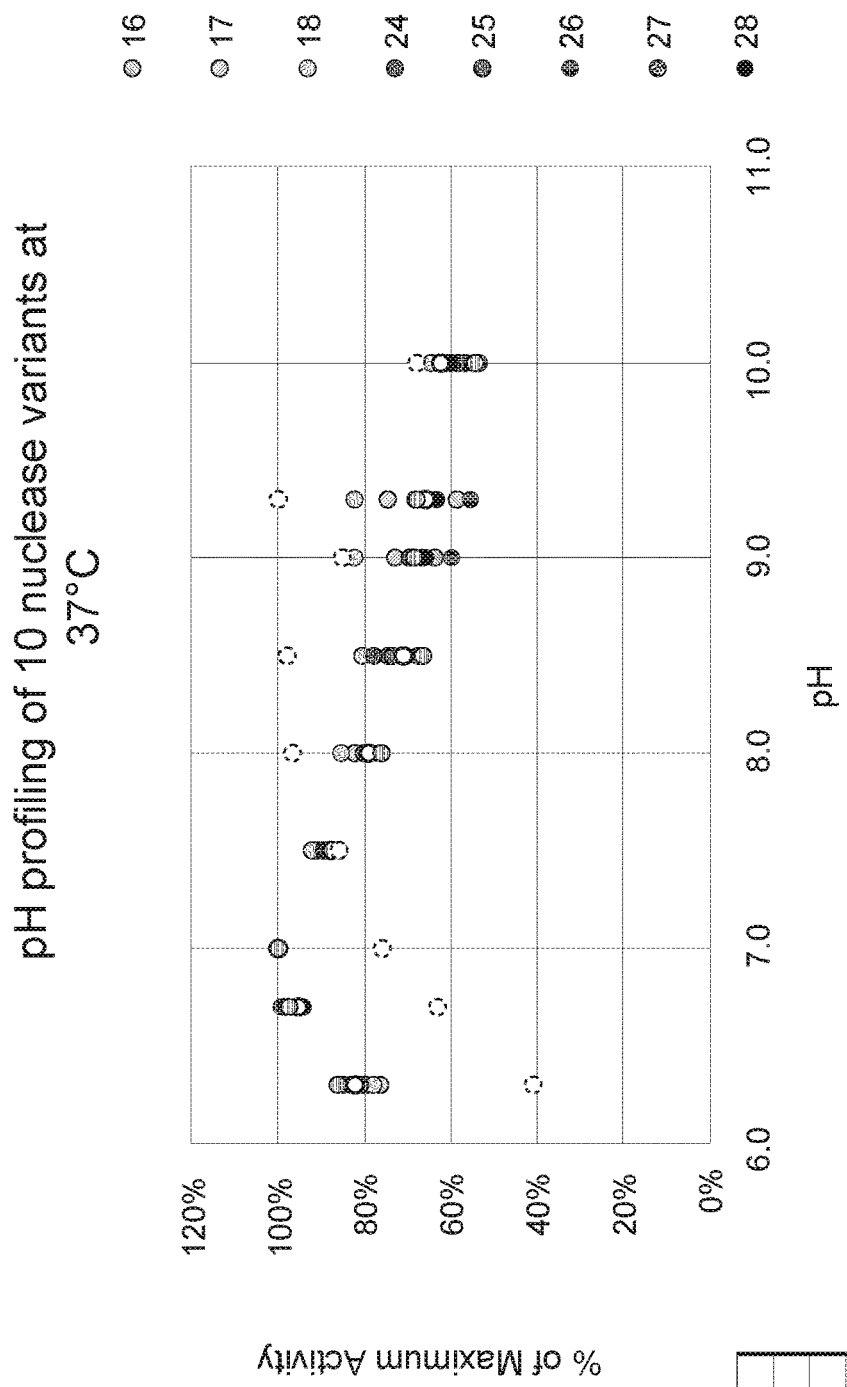
FIG. 3 shows pH profiling of ten nuclease variants at 37° C.

A number of nuclease variants generated by TMSCA were tested for pH profiling at 37° C. The test results are shown in Table 6 and FIG. 3.

TABLE 6

A260 reading results normalized to maximum activity for nuclease variants

| pH | VAR060 | VAR061 | VAR062 | VAR068 | VAR069 | VAR070 | VAR071 | VAR072 | VAR085 | VAR103 | PC | NC |
|---|---|---|---|---|---|---|---|---|---|---|---|---|
| 6.3 | 76.4 | 79.6 | 77.9 | 85.1 | 83.0 | 82.1 | 81.0 | 82.4 | 82.2 | 86.2 | 40.8 | |
| 6.7 | 95.3 | 97.9 | 95.4 | 97.8 | 98.5 | 99.2 | 94.8 | 94.3 | 95.4 | 97.5 | 63.1 | |
| 7.0 | 100.0 | 100.0 | 100.0 | 100.0 | 100.0 | 100.0 | 100.0 | 100.0 | 100.0 | 100 | 75.9 | |
| 7.5 | 91.2 | 91.0 | 92.3 | 89.6 | 88.9 | 88.2 | 85.9 | 87.1 | 87.8 | 87.6 | 85.9 | |
| 8.0 | 78.9 | 82.2 | 85.5 | 79.7 | 80.1 | 76.3 | 76.3 | 77.1 | 79.1 | 76.0 | 96.7 | |
| 8.5 | 71.4 | 74.4 | 80.6 | 77.8 | 73.6 | 66.9 | 67.5 | 70.1 | 71.0 | 66.4 | 98.0 | |
| 9.0 | 63.7 | 72.9 | 82.3 | 66.5 | 69.5 | 59.8 | 68.3 | 65.7 | 68.1 | 68.5 | 85.2 | |
| 9.3 | 58.5 | 74.6 | 82.3 | 65.9 | 68.2 | 55.4 | 68.0 | 63.2 | 65.8 | 67.9 | 100.0 | |
| 10.0 | 56.6 | 58.3 | 64.5 | 59.9 | 61.1 | 56.6 | 53.4 | 60.3 | 62.3 | 54.3 | 67.9 | |

Example 6

Nuclease Pretreatment of an Alpha Amylase Broth

Figure 4:
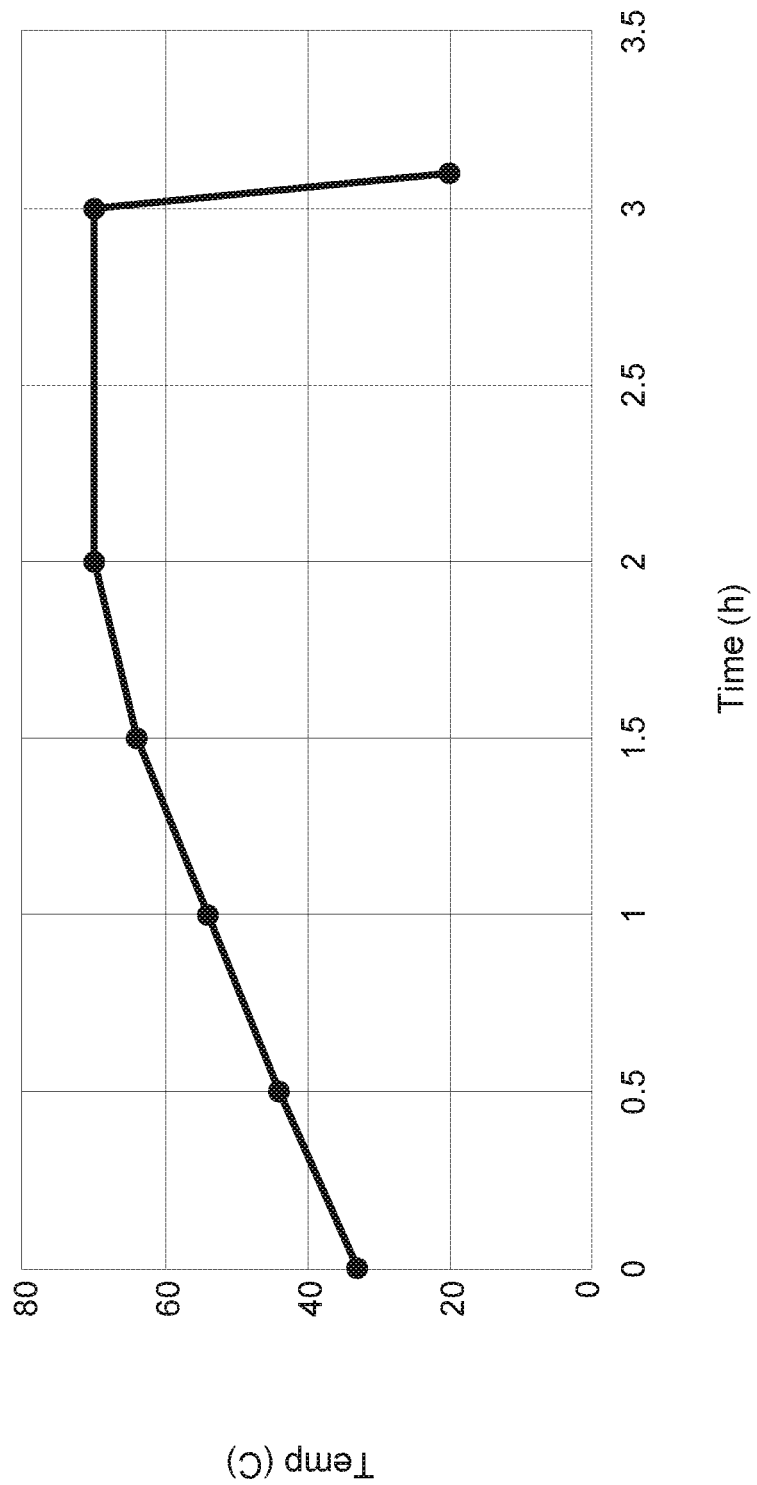
FIG. 4 is a plot showing heat kill temp ramp of an amylase.

Five lead variants VAR060, VAR062, VAR070, VAR072, and VAR085 were selected. For each of these five lead variants, heat kill of an alpha amylase broth was performed (see FIG. 4). Nuclease was added during the two hour ramping time of heat kill process.

Figure 5:
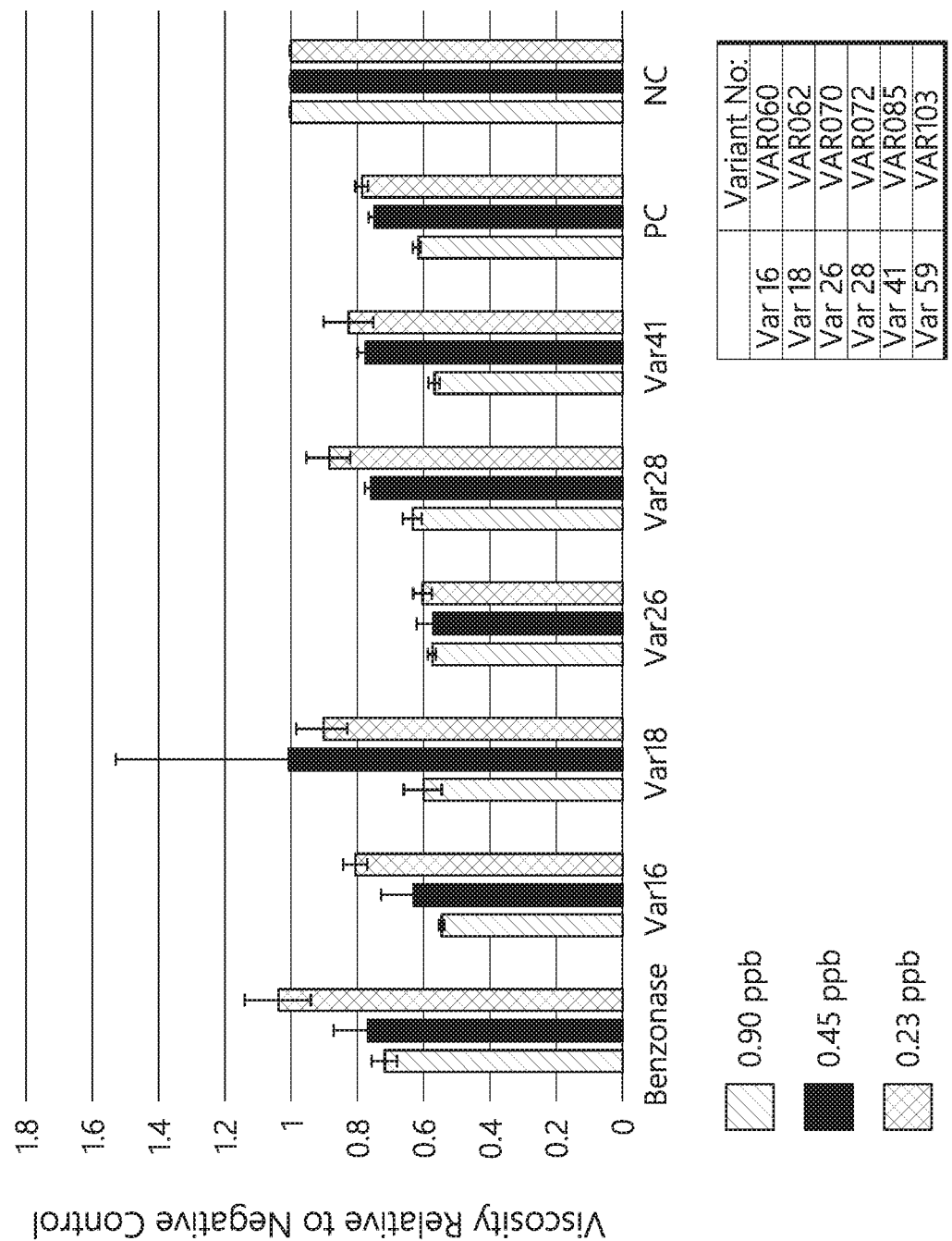
FIG. 5 shows normalized results of nuclease pretreatment of an amylase Broth.

The pretreatment results for the lead variants were normalized by nuclease concentration. Each variant was dosed at 3 levels in duplicate: 0.23 ppb, 0.45 ppb, and 0.9 ppb, which are equivalent to 250, 500, and 1000 U/L for Benzonase® endonuclease, respectively. Controls used for each dosing included: positive (the nuclease having the sequence of SEQ ID NO: 1), negative (vector control, diluted identically to parent), and Benzonase®. The un-normalized and normalized results of pretreatment are shown in FIG. 5, respectively. Among all the lead variants tested, VAR070 showed overall greatest viscosity reduction at each dose.

As shown in the examples disclosed herein, a number of nuclease variants having single point mutations have higher activity ratio 54 C°/37 C° compared to the parent nuclease while keeping similar specific activity. Also a number of nuclease variants having combinations of point mutations have an optimal temperature between 45 C°-55 C° (compared to 37 C° for the parent nuclease), and an optimal pH of about 6.5 compared to pH 8 for the parent nuclease.

The foregoing description and examples detail certain preferred embodiments of the description and describes the best mode contemplated by the inventors. It will be appreciated, however, that no matter how detailed the foregoing may appear in text, the description may be practiced in many ways and the description should be construed in accordance with the appended claims and any equivalents thereof. Although the present application has been described in detail above, it will be understood by one of ordinary skill in the art that various modifications can be made without departing from the spirit of the description.

In the present application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. Additionally, in this application, "and/or" denotes that both the inclusive meaning of "and" and, alternatively, the exclusive meaning of "or" applies to the list. Thus, the listing should be read to include all possible combinations of the items of the list and to also include each item, exclusively, from the other items. The addition of this term is not meant to denote any particular meaning to the use of the terms "and" or "or" alone. The meaning of such terms will be evident to one of skill in the art upon reading the particular disclosure.

All references cited herein including, but not limited to, published and unpublished patent applications, patents, text books, literature references, and the like, to the extent that they are not already, are hereby incorporated by reference in their entirety. To the extent that one or more of the incorporated literature and similar materials differ from or contradict the disclosure contained in the specification, including but not limited to defined terms, term usage, described techniques, or the like, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

What is claimed is:

1. A synthetic or recombinant polypeptide comprising an amino acid sequence having at least 80% sequence identity to SEQ ID NO: 1, wherein the polypeptide has nuclease activity, and wherein the polypeptide comprises one or more mutations of E230L, L114F, E260R, E230M, D246P, S161 R, N54S, T227H, E230R, G263A, G119N, V226K, N127S, P84V, D83E, D28G, V45T, M262V, A190K, P84N, 144R, G256S, A73M, P179L, Q135E, A60P, G263K, S161E, P72N, P84L, S74N, T82R, G75R, Q141R, and D107N.

2. The polypeptide of claim 1, wherein the one or more mutations are selected from the group consisting of
(T82R, L114F);
(T82R, L114F, G119N);
(T82R);
(T82R, G119N);
(L114F);
(L114F, G119N);
(G119N);
(G75R, T82R, L114F, G119N);
(G75R, T82R, L114F, G119N);
(G75R, T82R);
(G75R, L114F);
(G75R, L114F, G119N);
(S74N, G75R, T82R, G119N, Q141R);
(S74N, T82R, L114F, G119N);
(S74N, T82R, L114F, G119N, Q141R);
(S74N, T82R, Q141R);
(S74N, T82R, G119N, Q141R);
(S74N, L114F, Q141R);
(S74N, L114F, G119N, Q141R);
(S74N, Q141R);
(S74N, G75R, T82R, L114F, Q141R);
(S74N, G75R, T82R, L114F, G119N, Q141R);
(S74N, G75R, T82R, Q141R);
(S74N, G75R, L114F, Q141R);
(S74N, G75R, Q141R);
(I82R, D107N);
(G75R, T82R, D107N);
(D107N);
(G75R, T82R, G119N);
(I82R, D107N, G119N);
(G75R, T82R, D107N, G119N);
(D107N, G119N);
(G75R, D107N, G119N);
(S74N, T82R, D107N, Q141R);
(S74N, G75R, T82R, D107N, Q141R);
(S74N, G75R, D107N, Q141R);
(S74N, G119N, Q141R);
(S74N, G75R, G119N, Q141R);
(S74N, T82R, D107N, G119N, Q141R);
(S74N, G75R, T82R, D107N, G119N, Q141R);
(S74N, D107N, G119N, Q141R);
(S74N, G75R, D107N, G119N, Q141R);
(I82R, D107N, L114F);
(G75R, T82R, D107N, L114F);
(D107N, L114F);
(G75R, D107N, L114F);
(G75R, D107N);
(I82R, D107N, L114F, G119N);
(D107N, L114F, G119N);
(G75R, D107N, L114F, G119N);
(S74N, T82R, D107N, L114F, Q141R);
(S74N, G75R, T82R, D107N, L114F, Q141R);
(S74N, D107N, L114F, Q141R);
(S74N, G75R, D107N, L114F, Q141R);
(S74N, D107N, Q141R);
(S74N, G75R, L114F, G119N, Q141R);
(S74N, T82R, D107N, L114F, G119N, Q141R);
(S74N, G75R, T82R, D107N, L114F, G119N, Q141R);
(S74N, D107N, L114F, G119N, Q141R);
(S74N, G75R, D107N, L114F, G119N, Q141R); and
(G75R, T82R, D107N, L114F, G119N).

3. The polypeptide of claim 1, wherein the amino acid sequence of the polypeptide differs from the amino acid sequence of SEQ ID NO: 1 for comprising one or more mutations of E230L, L114F, E260R, E230M, D246P, S161R, N54S, T227H, E230R, G119N, V226K, G263A, N127S, P84V, D83E, D28G, V45T, M262V, A190K, P84N, 144R, G256S, A73M, P179L, Q135E, A60P, G263K, S161E, P72N, P84L, S74N, T82R, G75R, Q141R, and D107N.

4. The polypeptide of claim 1, wherein the polypeptide is more thermotolerant compared to the nuclease having the sequence of SEQ ID NO: 1.

5. The polypeptide of claim 1, wherein the nuclease activity of the polypeptide is at least 5% higher than that of the nuclease having the sequence of SEQ ID NO: 1 at 10° C. to 70° C.

6. The polypeptide of claim 1, the optimal temperature of the polypeptide is between 40° C. to 60° C.

7. The polypeptide of claim 1, wherein optimal pH of the polypeptide is between pH 4 to pH 11.

8. The polypeptide of claim 1, wherein the polypeptide comprises no signal sequence.

9. The polypeptide of claim 1, wherein the polypeptide comprises a signal sequence, and wherein the signal sequence is a heterologous sequence or a native signal sequence.

10. A composition comprising the polypeptide of claim 1.

11. The composition of claim 1, wherein the composition is a reaction mixture, a detergent composition, a detergent additive, a food, a food supplement, a feed supplement, a feed, a pharmaceutical composition, a fermentation product, a fermentation intermediate, a fermentation downstream reaction mixture, or a combination thereof.

12. The composition of claim 1, wherein the reaction mixture is for protein expression or purification.

13. A synthetic or recombinant nucleic acid that encodes the polypeptide of claim 1.

14. An expression vector comprising the nucleic acid of claim 13.

15. The expression vector of claim 14, wherein the expression vector comprises a viral vector, a plasmid, a phage, a phagemid, a cosmid, a fosmid, a bacteriophage, an artificial chromosome, or a combination thereof.

16. A recombinant cell comprising the polypeptide of claim 1, the nucleic acid of claim 13, the expression vector of claim 14, or a combination thereof.

17. The recombinant cell of claim 16, wherein the nucleic acid is a part of a chromosome of the recombinant cell, and wherein the cell is a bacterial cell, a mammalian cell, a fungal cell, a yeast cell, an insect cell, or a plant cell.

18. A method of producing a recombinant polypeptide having nuclease activity, comprising: expressing the nucleic acid of claim 1 under conditions that allow expression of the polypeptide, thereby producing recombinant polypeptide having nuclease activity, wherein the nucleic acid is operably linked to a promoter.

19. The method of claim 18, wherein the nucleic acid is present in an expression vector.

20. The method of claim 18, wherein the nucleic acid is present an in vitro expression system.

21. The method of claim 18, wherein the nucleic acid is present in a host cell to allow expression of the polypeptide, and wherein the host cell is a cell from an organism selected from the group consisting of *Pichia pastoris* (Komagataella *pastoris*), *Bacillus subtilis*, *Pseudomonas fluorescens*, Myceliopthora thermophile fungus, Tricodermea *reesei*, *Escherichia coli*, *Bacillus licheniformis*, *Aspergillus niger*, *Schizosaccharomyces pombe*, and *Sacaramyces cerevisiae*.

22. The method of claim 18, wherein the nucleic acid is a RNA molecule.

23. A method for degrading a polynucleotide, comprising contacting a polynucleotide molecule with the polypeptide of claim 1, thereby degrading the polynucleotide molecule.

24. The method of claim 23, wherein the polynucleotide molecule is a DNA molecule or a RNA molecule; and wherein the contacting occurs at pH 4 to pH 11 and at about 10° C. to about 70° C.

25. A method for washing an object, comprising contacting a composition comprising the polypeptide of claim 1 with the object under the conditions sufficient for said washing.

26. A method for degrading DNA or RNA during protein production, comprising culturing a host cell, wherein the host cell comprises a nucleic acid encoding a protein of interest; and expressing the polypeptide of claim 1 under conditions that allow degradation of DNA or RNA by the polypeptide.

27. The method of claim 26, wherein the host cell is a bacterial cell, a mammalian cell, a fungal cell, a yeast cell, a plant cell, or an insect cell.

28. The method of claim 26, wherein the polypeptide is expressed from an expression vector present in the host cell or the polypeptide is encoded by a nucleic acid sequence in a chromosome of the host cell.

29. The method of claim 26, wherein the polypeptide is expressed by cells that do not express the protein of interest.

30. The method of claim 26, wherein expression of one or more of the protein of interest and/or the polypeptide is inducible or non-inducible.

31. A reaction mixture, comprising:
the polypeptide of claim 1;
one or more nucleic acid molecules; and
an aqueous solution wherein the polypeptide hydrolyzes the one or more nucleic acid molecules.

32. The reaction mixture of claim 31, wherein the one or more nucleic acid molecules comprise single-stranded DNA molecules, double-stranded DNA molecules, single-stranded RNA molecules, double-stranded RNA molecules, or any combination thereof.

33. The reaction mixture of claim 31, wherein the one or more nucleic acid molecules are from a host cell for protein production.

34. The reaction mixture of claim 31, wherein the polypeptide is expressed in a host cell selected from the group consisting of bacterial cell, a mammalian cell, a fungal cell, a yeast cell, a plant cell, and an insect cell.

35. The reaction mixture of claim 31, wherein the nucleic acid and/or polypeptide is expressed by in vitro transcription or translation.

36. The reaction mixture of claim 31, wherein the reaction mixture has a temperature at about 10° C. to about 70° C.

37. The reaction mixture of claim 31, wherein the reaction mixture is at about pH 4 to about pH 11.

38. The reaction mixture of claim 31, wherein the aqueous solution is a detergent composition, a detergent additive, a food, a food supplement, a feed supplement, a feed, a pharmaceutical composition, a fermentation product, a fermentation intermediate, a fermentation downstream reaction mixture, a product from protein production process, an intermediate from protein production process, or a protein purification solution.

39. A method for degrading DNA or RNA in a protein production mixture, comprising culturing a host cell, wherein the host cell comprises a nucleic acid encoding a protein of interest; and expressing the polypeptide of claim 1 under conditions that allow degradation of DNA or RNA by the polypeptide.

40. The method of claim 39, wherein the host cell is a bacterial cell, a mammalian cell, a fungal cell, a yeast cell, a plant cell, or an insect cell.

41. The method of claim 39, wherein the polypeptide is expressed from an expression vector present in the host cell or the polypeptide is encoded by a nucleic acid sequence in a chromosome of the host cell.

42. The method of claim 39, wherein the polypeptide is expressed by cells that do not express the protein of interest.

43. The method of claim 39, wherein expression of one or more of the protein of interest and/or the polypeptide is inducible or non-inducible.

44. A method for degrading DNA or RNA during protein production, comprising: culturing a host cell, wherein the host cell comprises a nucleic acid encoding a protein of interest; and adding a polypeptide of claim 1 under conditions that allow degradation of DNA or RNA by the polypeptide.

45. The method of claim 44, wherein the host cell is a bacterial cell, a mammalian cell, a fungal cell, a yeast cell, a plant cell, or an insect cell.

* * * * *

SEQUENCE LISTING

```
<160> NUMBER OF SEQ ID NOS: 2

<210> SEQ ID NO 1
<211> LENGTH: 266
<212> TYPE: PRT
<213> ORGANISM: Artificial Sequence
<220> FEATURE:
<223> OTHER INFORMATION: Nuclease

<400> SEQUENCE: 1

Met Arg Phe Asn Asn Lys Met Leu Ala Leu Val Ala Leu Leu Phe Ala
1               5                   10                  15

Ala Gln Ala Ser Ala Asp Thr Leu Glu Ser Ile Asp Asn Cys Ala Val
            20                  25                  30

Gly Cys Pro Thr Gly Gly Ser Ser Asn Val Ser Ile Val Arg His Ala
        35                  40                  45

Tyr Thr Leu Asn Asn Ser Thr Thr Lys Phe Ala Asn Trp Val Ala
    50                  55                  60

Tyr His Ile Thr Lys Asp Thr Pro Ala Ser Gly Lys Thr Arg Asn Trp
65                  70                  75                  80

Lys Thr Asp Pro Ala Leu Asn Pro Ala Asp Thr Leu Ala Pro Ala Asp
                85                  90                  95

Tyr Thr Gly Ala Asn Ala Ala Leu Lys Val Asp Arg Gly His Gln Ala
            100                 105                 110

Pro Leu Ala Ser Leu Ala Gly Val Ser Asp Trp Glu Ser Leu Asn Tyr
        115                 120                 125

Leu Ser Asn Ile Thr Pro Gln Lys Ser Asp Leu Asn Gln Gly Ala Trp
    130                 135                 140

Ala Arg Leu Glu Asp Gln Glu Arg Lys Leu Ile Asp Arg Ala Asp Ile
145                 150                 155                 160

Ser Ser Val Tyr Thr Val Thr Gly Pro Leu Tyr Glu Arg Asp Met Gly
                165                 170                 175

Lys Leu Pro Gly Thr Gln Lys Ala His Thr Ile Pro Ser Ala Tyr Trp
            180                 185                 190

Lys Val Ile Phe Ile Asn Asn Ser Pro Ala Val Asn His Tyr Ala Ala
        195                 200                 205

Phe Leu Phe Asp Gln Asn Thr Pro Lys Gly Ala Asp Phe Cys Gln Phe
    210                 215                 220

Arg Val Thr Val Asp Glu Ile Glu Lys Arg Thr Gly Leu Ile Ile Trp
225                 230                 235                 240

Ala Gly Leu Pro Asn Asp Val Gln Ala Ser Leu Lys Ser Lys Pro Gly
                245                 250                 255

Val Leu Pro Glu Leu Met Gly Cys Lys Asn
            260                 265

<210> SEQ ID NO 2
<211> LENGTH: 798
<212> TYPE: DNA
<213> ORGANISM: Artificial Sequence
<220> FEATURE:
<223> OTHER INFORMATION: Nuclease
```

```
<400> SEQUENCE: 2
atgcgcttta acaataaaat gctggcactc gtagcgctgc tgtttgcggc gcaggcgtcc      60
gcagatacac tggagagcat tgacaactgc gccgtgggct gcccgaccgg cggttctagc     120
aatgttagta tcgtccgcca tgcgtatact ctgaataaca actccaccac caaatttgcc     180
aactgggtgg cgtatcacat tactaaagac acacctgcgt caggcaagac tcgtaattgg     240
aaaactgatc cagcgttgaa tcctgctgac accctggctc cggcggatta taccggcgct     300
aatgccgctc ttaaagtgga tcgtgggcac caggcgccgc ttgcgagcct ggcgggtgtt     360
tcagactggg aaagcctgaa ttacctctca aacatcacgc cgcagaaaag tgatctgaat     420
caaggcgcgt gggcccgtct ggaggatcag gagcgcaaac ttatcgatcg tgcagatatt     480
agtagtgtgt atactgtcac gggcccactg tacgaacgtg atatgggcaa actcccgggc     540
acccagaaag ctcacactat tccgtctgcg tactggaaag tgatctttat taacaactcc     600
ccggcggtga atcattacgc tgcgtttttg tttgatcaga acaccccaaa aggggcggat     660
ttctgccagt ttcgtgttac cgttgatgaa attgaaaaac gcacaggctt aattatctgg     720
gcgggcctgc caaatgacgt ccaggcgtcc ttgaaatcca agccgggcgt gctgccggaa     780
ctgatgggtt gcaaaaac                                                   798
```